US010085908B2

(12) United States Patent
Lee et al.

(10) Patent No.: US 10,085,908 B2
(45) Date of Patent: Oct. 2, 2018

(54) HOLDER AND WALKING ASSISTANT ROBOT HAVING THE SAME

(71) Applicant: Samsung Electronics Co., Ltd., Suwon-si, Gyeonggi-do (KR)

(72) Inventors: Youn Baek Lee, Yongin-si (KR); Yong Jae Kim, Seoul (KR); Jeong Hun Kim, Hwaseong-si (KR); Se Gon Roh, Suwon-si (KR); Min Hyung Lee, Anyang-si (KR); Jong Won Lee, Uiwang-si (KR); Byung June Choi, Gunpo-si (KR); Hyun Do Choi, Yongin-si (KR); Young Do Kwon, Yongin-si (KR); Tae Jun Sang, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 536 days.

(21) Appl. No.: 14/598,785

(22) Filed: Jan. 16, 2015

(65) Prior Publication Data

US 2015/0209215 A1 Jul. 30, 2015

(30) Foreign Application Priority Data

Jan. 24, 2014 (KR) ........................ 10-2014-0009064

(51) Int. Cl.
*A61H 3/00* (2006.01)
*A61H 1/02* (2006.01)
*A61F 5/01* (2006.01)

(52) U.S. Cl.
CPC ............. *A61H 3/00* (2013.01); *A61F 5/0102* (2013.01); *A61H 1/024* (2013.01); *A61H 1/0237* (2013.01);

(Continued)

(58) Field of Classification Search
CPC .......... A61H 1/00; A61H 1/02; A61H 1/0237; A61H 1/024; A61H 1/0244; A61H 1/0251;

(Continued)

(56) References Cited

U.S. PATENT DOCUMENTS

| 39,578 A | * | 8/1863 | Kimball | .................. A61F 2/588 |
| | | | | 623/57 |
| 984,179 A | * | 2/1911 | Aydt | ....................... A61F 2/583 |
| | | | | 623/64 |

(Continued)

FOREIGN PATENT DOCUMENTS

| EP | 2399472 A1 | 12/2011 |
| JP | 2001-213379 A | 8/2001 |

(Continued)

OTHER PUBLICATIONS

European Search Report dated Jun. 16, 2015 for EP Application No. 15 15 2169.

(Continued)

*Primary Examiner* — Quang D Thanh
(74) *Attorney, Agent, or Firm* — Harness, Dickey & Pierce, P.L.C.

(57) ABSTRACT

A holder may be more easily mounted on a user's body by applying tension to a cable. An inner side surface of the holder with which the user's body comes in contact transmits uniform pressure to the user's body such that the holder may be more comfortable to the user.

18 Claims, 17 Drawing Sheets

(52) U.S. Cl.
CPC ......... *A61H 1/0244* (2013.01); *A61H 1/0255* (2013.01); *A61H 1/0266* (2013.01); *A61H 3/008* (2013.01); *A61H 2201/0103* (2013.01); *A61H 2201/0192* (2013.01); *A61H 2201/1215* (2013.01); *A61H 2201/1246* (2013.01); *A61H 2201/163* (2013.01); *A61H 2201/164* (2013.01); *A61H 2201/165* (2013.01); *A61H 2201/169* (2013.01); *A61H 2201/1628* (2013.01); *A61H 2201/1642* (2013.01); *A61H 2201/5007* (2013.01); *A61H 2201/5061* (2013.01); *A61H 2230/08* (2013.01)

(58) Field of Classification Search
CPC ................ A61H 1/0255; A61H 1/0262; A61H 2001/0211; A61H 2001/0248; A61H 2205/10; A61H 2205/102; A61H 2205/088; A61H 2205/106; A61H 2205/108; A61H 2203/0406; A61H 3/00; A61H 1/0266; A61H 3/008; A61H 2201/5061; A61H 2201/169; A61H 2201/164; A61H 2201/1628; A61H 2201/1246; A61F 2220/00; A61F 2220/0091; A61F 5/04; A61F 5/05; A61F 5/058; A61F 5/05825; A61F 5/05841; A61F 5/0585; A61F 5/05858; A61F 5/0102
USPC .......................................... 602/6, 12, 16, 23
See application file for complete search history.

(56) References Cited

U.S. PATENT DOCUMENTS

| | | | | |
|---|---|---|---|---|
| 3,625,200 | A * | 12/1971 | Muller ................. | A61B 1/0055 600/585 |
| 4,128,921 | A | 12/1978 | Heinze et al. | |
| 4,144,881 | A * | 3/1979 | Chappell .................... | A61F 2/30 602/16 |
| 4,573,455 | A * | 3/1986 | Hoy ....................... | A61F 5/0123 602/16 |
| 4,649,906 | A | 3/1987 | Spademan | |
| 4,685,929 | A * | 8/1987 | Monestier ............... | A61F 2/583 623/64 |
| 4,821,532 | A * | 4/1989 | Jaques ................... | A44C 5/025 224/178 |
| 4,961,544 | A * | 10/1990 | Bidoia .................... | A43B 5/0449 24/68 SK |
| 5,005,558 | A * | 4/1991 | Aomori ................ | A61B 1/0055 600/141 |
| 5,178,137 | A * | 1/1993 | Goor ..................... | A61F 5/0111 601/40 |
| 5,197,767 | A * | 3/1993 | Kimura ................... | F16G 13/10 138/120 |
| 5,297,443 | A * | 3/1994 | Wentz .................. | B05B 15/066 446/27 |
| 5,448,989 | A * | 9/1995 | Heckele ................ | A61B 1/0055 600/104 |
| 5,791,338 | A * | 8/1998 | Merchant .......... | A61M 16/0488 128/200.26 |
| 5,934,599 | A * | 8/1999 | Hammerslag ............ | A43C 1/00 242/396.1 |
| 6,418,706 | B1 * | 7/2002 | Kit .......................... | A44C 5/10 59/80 |
| 7,654,973 | B2 * | 2/2010 | Firsov ..................... | A61F 5/026 128/869 |
| 7,935,068 | B2 * | 5/2011 | Einarsson ............. | A61F 5/0102 602/1 |
| 7,993,296 | B2 * | 8/2011 | Nordt, III ............. | A61F 5/0118 602/20 |
| 9,204,985 | B1 * | 12/2015 | Fullerton .............. | A61F 5/0104 |
| 9,610,185 | B2 * | 4/2017 | Capra ................... | A61F 5/0102 |
| 2001/0008952 | A1 * | 7/2001 | Takada ................... | A61B 1/121 600/155 |
| 2003/0204938 | A1 | 11/2003 | Hammerslag | |
| 2006/0020237 | A1 | 1/2006 | Nordt et al. | |
| 2006/0058582 | A1 * | 3/2006 | Maahs ............... | A61B 1/00154 600/144 |
| 2006/0173391 | A1 * | 8/2006 | Bodenschatz ........... | A61F 5/058 602/12 |
| 2011/0098618 | A1 | 4/2011 | Fleming | |
| 2011/0172570 | A1 | 7/2011 | Shimizu et al. | |
| 2013/0110020 | A1 | 5/2013 | Ingimundarson et al. | |
| 2014/0005798 | A1 | 1/2014 | Bache et al. | |

FOREIGN PATENT DOCUMENTS

| | | |
|---|---|---|
| JP | 2011019718 A | 2/2011 |
| JP | 2013039656 A | 2/2013 |
| KR | 20010062557 A | 7/2001 |
| KR | 20110124924 A | 11/2011 |

OTHER PUBLICATIONS

Japanese Office Action dated Jan. 30, 2018 for JP Patent Application No. 2014-245044.
The State Intellectual Property Office of P.R. China Office Action dated Feb. 12, 2018 for CN Application No. 201510035905.7.
Office Action dated May 16, 2018 by the European Patent Office for EP Application No. 15 152 169.7.

* cited by examiner

HOLDER AND WALKING ASSISTANT ROBOT HAVING THE SAME

CROSS-REFERENCE TO RELATED APPLICATION

This application claims the benefit of Korean Patent Application No. P2014-9064, filed on Jan. 24, 2014 in the Korean Intellectual Property Office, the entire disclosure of which is incorporated herein by reference.

BACKGROUND

1. Field

Example embodiments of relate to a holder configured to uniformly transmit force to a wide area and a walking assistant robot having the same.

2. Description of the Related Art

Walking assistant robots may have various uses. For example, walking assistant robots may be used as an assistant device for aiding a user having decreased muscular strength, and as a power assist robot for amplifying a user's muscular strength and supporting a load of a heavy object instead of the user, for example, carrying the heavy object.

SUMMARY

Example embodiments relate to a holder and a walking assistant robot having the same. In at least some example embodiments, the holder includes a plurality of links that are configured to transmit uniform force to a contact surface of a body.

According to some example embodiments, the holder is configured to mount on a user's body.

The holder may include a link assembly in which a plurality of links are connected to wrap around the user's body; a cable installed in the link assembly and configured to adjust an angle between any link included in the link assembly and another adjacent link due to adjustable tension; and a holder main body on which one side of the cable is mounted.

The holder main body may include a manipulating unit capable of adjusting tension applied to the cable by extending or shortening the cable.

When the cable is shortened by manipulating the manipulating unit, tension of the cable may increase and an angle between adjacent links may decrease.

When a length of the cable increases by manipulating the manipulating unit, an angle between adjacent links may increase.

One side of the cable may be fixed in a shaft provided in the holder main body, and a gear unit may be connected to the shaft.

The gear unit may receive driving force from the manipulating unit and rotate such that the cable is wrapped around or released from the shaft, thereby shortening or extending the cable.

The holder main body may further include a locking unit configured to interfere with an operation of the gear unit connected to the shaft.

The locking unit may include a locking gear that is selectively meshed with the gear unit.

When the locking gear is meshed with the gear unit, rotation of the gear unit in a specific direction may be interfered with.

When the locking gear is meshed with the gear unit, rotation of the gear unit in a direction in which the cable is released from the shaft may be interfered with.

When meshing of the locking gear with the gear unit is released, the gear unit may rotate in a clockwise or counterclockwise direction so that the cable is wrapped around or released from the shaft.

The plurality of links may be pivotably connected by a pin.

The holder may include a wire that passes through the link assembly and maintains a shape of the link assembly.

A distance between a straight line extending in a direction in which the pin extends and the cable may become shorter from a side of the manipulating unit to an end of the link assembly.

The plurality of links may be connected by a panel having elasticity.

A distance between the panel and the cable may become shorter from the manipulating unit side to the end of the link assembly.

The link assembly may be connected to left and right sides of the manipulating unit.

According to other example embodiments, the walking assistant robot may be mounted on a user's body and configured to aid walking of the user.

The robot may include a frame configured to come in close contact with the user's body by connecting a plurality of links; and a holder configured to mount the frame on the user's body, wherein the holder includes; a holder main body to be mounted on the frame; a link assembly in which the plurality of links are connected and that extends from the holder main body; and a cable that is installed in the link assembly and is extended or shortened to adjust a curvature of the link assembly.

One side of the cable may be fixed in a shaft provided in the holder main body, and the holder main body may include a manipulating unit capable of rotating the shaft.

When the shaft rotates in one direction, the cable may be wrapped around the shaft, thereby decreasing a length of the cable, and when the shaft rotates in the other direction, the cable may be released from the shaft, thereby increasing the length of the cable.

The holder main body may include a locking unit configured to interfere with rotation of the shaft in the other direction.

The locking unit may include a locking switch, and a state in which the locking unit interferes with the shaft may be released by manipulating the locking switch.

A fixing pin may be installed in a link located in an end of the link assembly and a location of the cable in the link may be fixed by the fixing pin.

The plurality of links may be pivotably connected by a pin and a wire having elasticity may be installed in the plurality of links.

The plurality of links may be connected by a panel having elasticity.

According to still other example embodiments, a holder may be mounted on a walking assistant robot.

The holder may include a link assembly configured to wrap around a user's body by connecting a plurality of links; a holder main body configured to mount the link assembly on the walking assistant robot; a cable configured to connect the plurality of links forming the link assembly and bend the link assembly due to adjustable tension; a manipulating unit mounted on the holder main body and configured to adjust tension applied to the cable by extending or shortening the cable; and a locking unit configured to interfere with an operation of the manipulating unit in a direction in which the cable extends.

In the link assembly, a minimum distance between an inner side surface of each link and the cable may be the same.

The plurality of links may be pivotably connected by a pin penetrating two adjacent links.

A minimum distance between the pin and the cable may become shorter from the holder main body to an end of the link assembly.

In the link assembly, an object that connects the plurality of links and has elasticity may be mounted on.

Some example embodiments may be related to a walking assistance robot configured to assist a user with walking.

In some example embodiments, the walking assistance robot may include a walking assistive device having an exoskeleton shape such that the walking assistance device is configured to attach to one or more legs of the user via at least one holder. The holder may include a plurality of interconnected links configured to attach to the legs of the user; a cable configured to adjust an angle between adjacent ones of the links in response to tension applied thereto; and a tension device configured to apply the tension to the cable.

In some example embodiments, the tension device is configured to vary an amount of tension applied to the cable.

In some example embodiments, the tension device includes a gear having a shaft extending therefrom, the gear connected to an adjuster, the tension device configured to vary the amount of tension applied to the cable by winding the cable around the shaft in response to the user manipulating the adjuster.

In some example embodiments, the tension device includes a sensor configured to detect when the user is walking; and a processor configured to instruct a driver to vary the amount of tension applied to the cable based on whether the user is walking.

In some example embodiments, the tension device is configured to apply the tension such that a net torque applied to the links is in equilibrium, the net torque including a force associated with the tension and a force associated with a counter force applied by the legs of the user.

In some example embodiments, the holder is configured to apply the force associated with the tension to the legs of the user such that the force associated with the tension is applied uniformly around a circumference of the legs of the user.

BRIEF DESCRIPTION OF THE DRAWINGS

These and/or other aspects of the example embodiments will become apparent and more readily appreciated from the following description of some of the example embodiments, taken in conjunction with the accompanying drawings of which.

DETAILED DESCRIPTION

Figure 1:
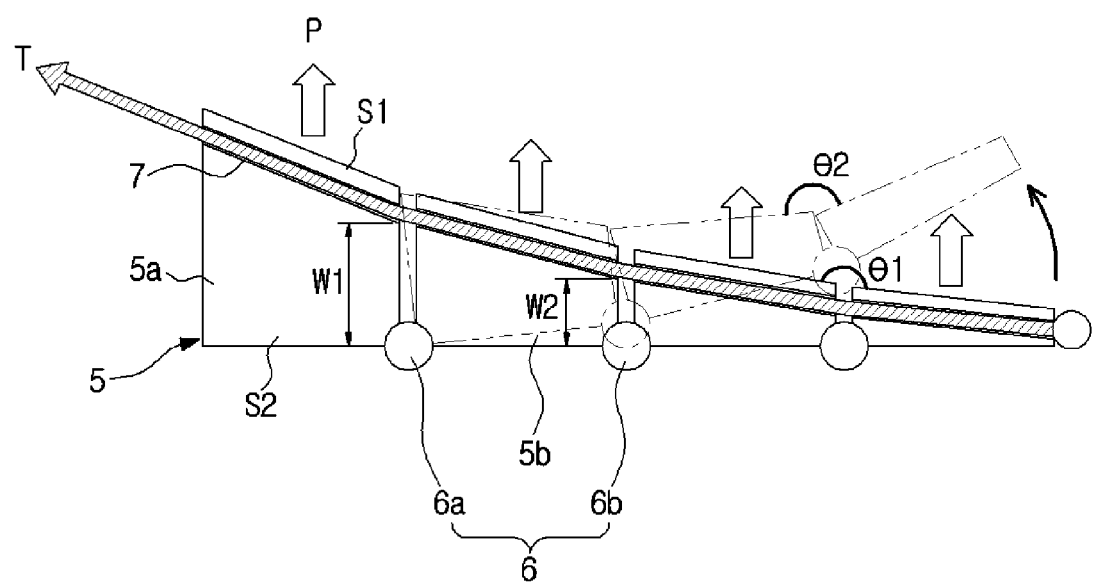
FIG. 1 is a conceptual diagram according to some example embodiments.

Hereinafter, a holder according to some example embodiments and a walking assistant robot having the same will be described in detail with reference to the drawings.

Example embodiments will now be described more fully with reference to the accompanying drawings, in which some example embodiments are shown. In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 is a conceptual diagram according to some example embodiments.

As illustrated in FIG. 1, a holder 5 is configured to mount on a portion of a body. The holder 5 may be formed by pivotably connecting a plurality of links. The plurality of links may be pivotably connected by pins 6. For example, a first link 5a and a second link 5b may be connected by a first pin 6a and the second link 5b and a subsequent link may be connected by a second pin 6b.

The holder 5 may be formed such that the plurality of links wrap around the body by tension exerted on a cable 7. The cable 7 may be formed so as to pass through the plurality of links. One end of the cable 7 may be fixed in a link provided in an end of the holder 5. Tension may be applied to the cable 7 through the other end of the cable 7. When the tension is applied to the cable 7, the plurality of links may be pulled to wrap around the body by the cable 7. A first angle ($\theta 1$) formed by inner side surfaces of adjacent links before the tension is applied to the cable 7 may be greater than a second angle ($\theta 2$) formed by inner side surfaces of adjacent links after the tension is applied to the cable 7.

For example, the plurality of links forming the holder 5 include a first link 5a and a second link 5b. The first link 5a and the second link 5b may be pivotably connected by one of the pins 6. The cable 7 may be formed so as to pass through the plurality of links including the first link 5a and the second link 5b such that a minimum distance between the cable 7 and an inner side surface S1 of the links is the same.

A second minimum distance W2 between the cable 7 and the pin 6b, which connects a link located farther from a driving source configured to provide the tension to the cable 7 and a link adjacent thereto, may be shorter than a first minimum distance W1 between the cable 7 and the first pin 6a, which connects a link located closer to the driving source and a link adjacent thereto (e.g. the first link 5a and the second link 5b). In this case, the pin 6 of the link may be located in an outer side surface S2 side.

As discussed above, one side of the cable 7 may be fixed in a link provided in an end of the holder 5. When the other side of the cable 7 is pulled by a user's manipulation, the plurality of links may receive a driving force that wraps the holder 5 around the user's body.

When the plurality of links are pulled by the cable 7 and wrap around the user's body, an inner side surface of each link may press the user's body. In this case, force exerted on the user's body by the inner side surface of each link may be distributed and transmitted. For example, the inner side surface of the link may transmit a uniform pressure (P) to the user's body. Accordingly, the holder 5 may be mounted on the user's body, such that the holder 5 is comfortable for the user to wear and does not provide discomfort to the user due to pressure concentration in force transmission.

The minimum distance W1 between the pin 6 mounted on the link and the cable 7 becomes shorter from the other side to one side of the cable 7 such that moment of the pin 6 due to force exerted on the user's body by the inner side surface of each link and moment of the pin 6 due to tension applied to the cable 7 may be balanced.

Figure 2:
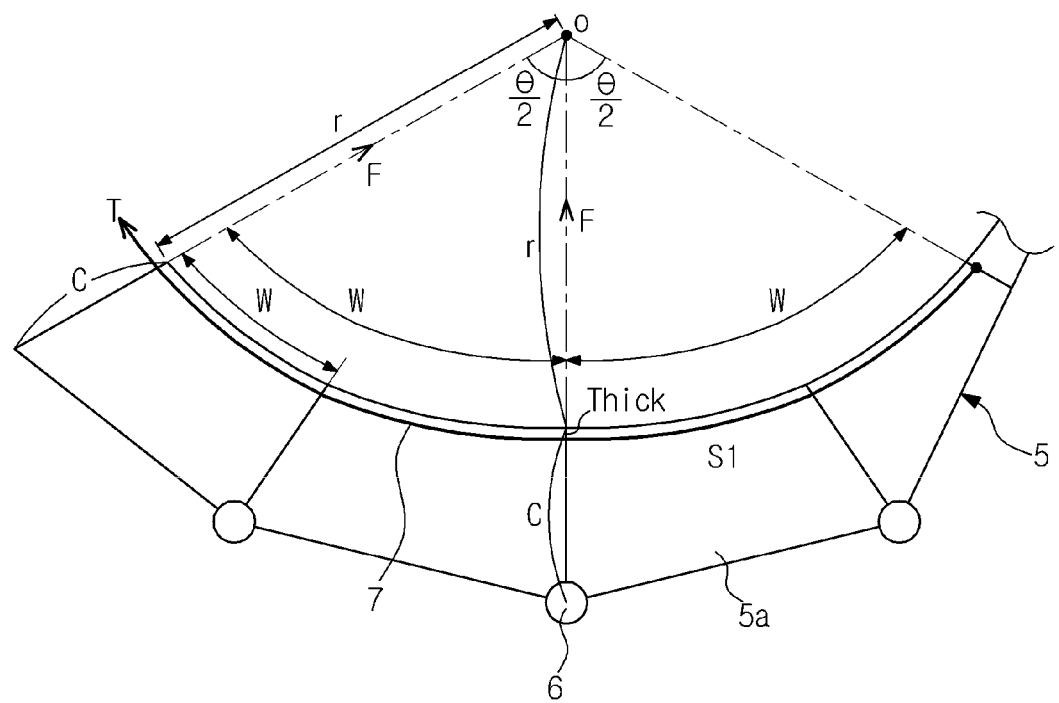
FIG. 2 is a diagram illustrating a concept of distributing and transmitting of force exerted by a holder to a body.

FIG. 2 is a diagram illustrating a concept of distributing and transmitting of force exerted by the holder to the body.

As illustrated in FIG. 2, at least a part of the holder 5 transmits force F to the user's body. The force F may be a vector having a direction toward a center point O located inside the user's body on which the holder 5 is mounted.

A sector of the holder 5 that is symmetrical around the center point O may have an angle $\theta$, the sector may be divided into two halves that each have a width of 2w such that the sector is made of four links. A distance between the inner side surface S1 of the holder 5 and the center point O may be a distance r. For example, when the holder 5 is mounted on the user's thigh, r may be a radius of the user's thigh.

A distance, for example a minimum distance, between the inner side surface S1 of the holder 5 with which the user's body comes in contact and the cable 7 may be a distance Thick. Further, a distance, for example, a minimum distance, between the cable 7 and the pin 6 may be a distance c.

When the force F is transmitted to the user's body by the holder 5, a pressure transmitted by the holder 5 to the user's body may be a, and tension of the cable 7 mounted on the holder 5 may be T.

The force F applied by the holder 5 to the user's body may satisfy Equation 1, shown below.

$$F = -2\int_0^{\frac{\theta}{2}} \sigma rw dq \cos q = 2\sigma rw \int_0^{\frac{\theta}{2}} \cos q dq = 2\sigma rw \sin\frac{\theta}{2} \qquad \text{Equation 1}$$

In the pin 6, when moment due to tension T of the cable 7 and moment due to the force F applied by the holder 5 to the user's body are balanced, the force F may satisfy Equation 2, shown below.

$$F(r + c + \text{Thick})\sin\frac{\theta}{2} = Tc \qquad \text{Equation 2}$$

When the force F of Equation 1 is substituted into Equation 2 and solved, Equation 3, shown below, may be obtained.

$$Tc = \left(2\sigma rw \sin\frac{\theta}{2}\right)(r + c + \text{Thick})\sin\frac{\theta}{2} \qquad \text{Equation 3}$$

When Equation 3 is solved for the distance c, Equation 4, shown below, may be obtained.

$$c = \frac{2\sigma r(r + \text{Thick})w\left(\sin\frac{\theta}{2}\right)^2}{T - 2\sigma rw\left(\sin\frac{\theta}{2}\right)^2} \quad \text{Equation 4}$$

In order to transmit the force F by the inner side surface of the holder 5 to the user's body, the holder 5 may be designed such that the minimum distance c between the cable 7 and the pin 6 may satisfy Equation 4.

The minimum distance c between the cable 7 and the pin 6 may decrease when a distance from the driving source configured to transmit the tension to the cable 7 to the pin 6 increases.

When the minimum distance c between the cable 7 and the pin 6 is set as Equation 4, the force F exerted on the user's body by the holder 5 due to the tension T of the cable 7 may be distributed and transmitted through the entire inner side surface of the holder 5. Accordingly, the holder 5 may reduce the user's discomfort by providing uniform pressure by the holder 5.

Figure 3:
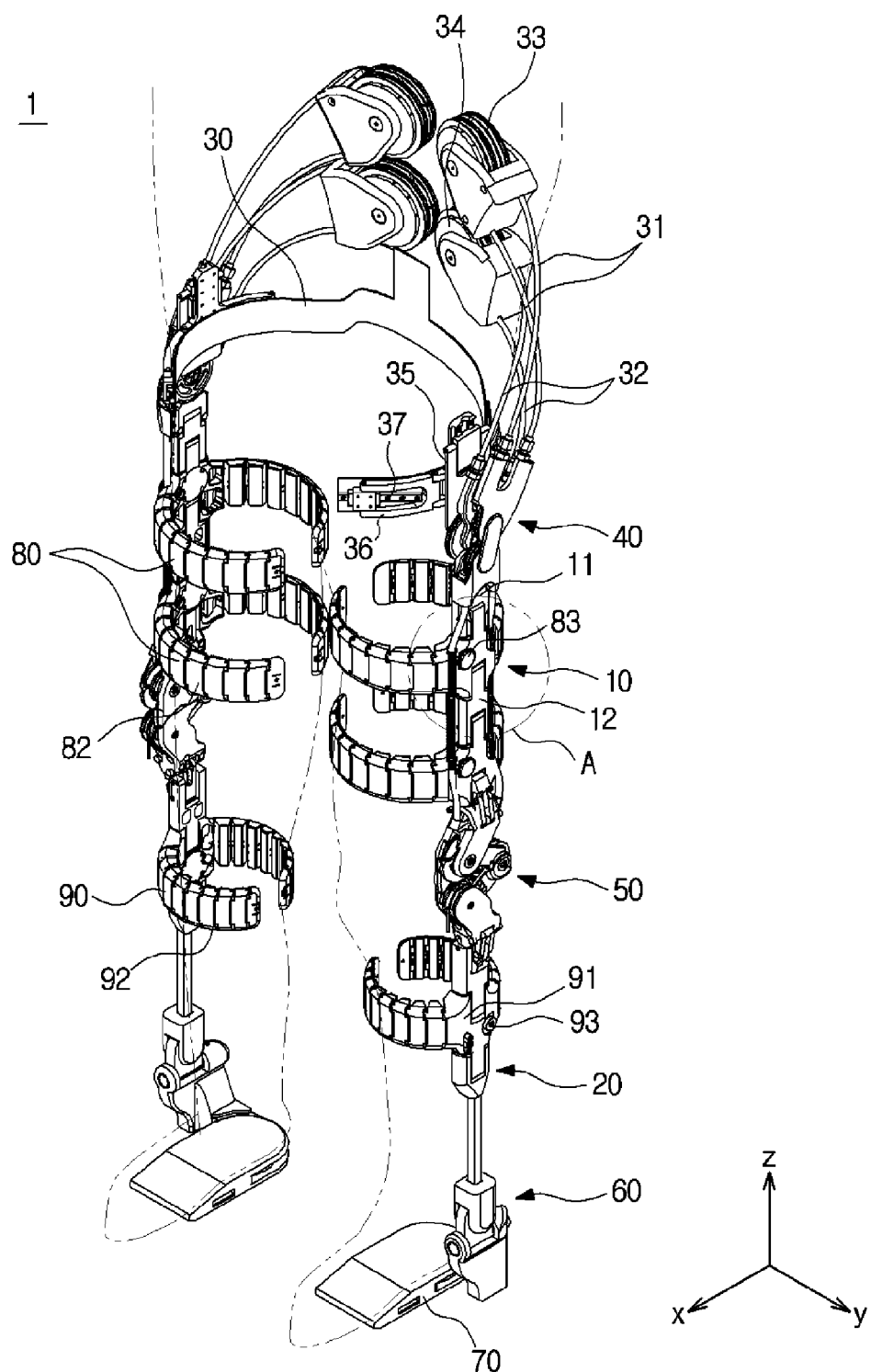
FIG. 3 is a diagram illustrating a walking assistant robot according to some example embodiments.

FIG. 3 is a diagram illustrating a walking assistant robot according to some example embodiments.

As illustrated in FIG. 3, a walking assistant robot 1 according to some example embodiments may include frames 10 and 20 configured to extend in a length direction of the user's leg and support the user's load. The frames 10 and 20 may include a first frame 10 configured to support the user's femoral region and a second frame 20 configured to support the user's calf.

At least one of the first frame 10 and the second frame 20 may be provided by connecting the plurality of frame links. For example, the first frame 10 may be provided by connected at least a first frame link 11 and a second frame link 12.

The first frame 10 may bend flexibly according to a curvature of the femoral region on which the frame is mounted. The second frame 20 may bend flexibly according to a curvature of the calf on which the frame is mounted. For example, the first frame 10 or the second frame 20 may bend flexibly and stably support the user's load.

A waist fixing device 30 configured to attach on the user's waist may be connected to the first frame 10. The first frame 10 may be pivotably connected to the waist fixing device 30 by a robotic hip joint 40. The first frame 10 and the second frame 20 may be pivotably connected by a robotic knee joint 50. A foot structure 70 configured to attach on the user' foot may be connected to the second frame 20. The second frame 20 and the foot structure 70 may be pivotably connected by a robotic ankle joint 60.

The walking assistant robot 1 may further include a driving source and a control unit. The driving source may be configured to provide driving force to the hip joint 40 and/or the knee joint 50 and the control unit may be configured to control an operation of the walking assistant robot 1. A sensor may be provided in the foot structure 70. The sensor may be configured to detect information on the user's motion and transmit the detected information to the control unit, and the control unit may control an operation of the hip joint 40 or the knee joint 50 using the transmitted information.

The first frame 10 may be pivoted with three degrees of freedom (DOFs). A DOF may mean the number of independent motions of a mechanism, or the number of independent parameters that are required to specify an independent motion at a relative position with respect to links. For example, an object that is in a 3Dimensional (3D) space composed of x-, y-, and z-axes has one or more DOF of 3 DOF (positions on the respective axes) to specify a spatial position of the object, and 3 DOF (rotation angles with respect to the respective axes) to specify a spatial orientation of the object. If a certain object is movable on the individual axes and rotatable with respect to the individual axes, the object may be understood to have 6 DOF.

A first wire 31 may wrap around a pulley 33 connected to the driving source, and the first wire 31 may be connected to the first frame 10 through the hip joint 40. The first frame 10 may be pivoted by shortening or extending the first wire 31. For example, when the driving source rotates the pulley 33 to wrap the first wire 31 around the pulley 33, the first frame 10 may be pivoted around a y axis in a first direction. When the driving source rotates the pulley 33 to release the first wire 31 from the pulley 33, the first frame 10 may be pivoted around the y axis in a second direction opposite to the first direction.

The hip joint 40 may rotate around an x axis by a hinge device 35. When the hip joint 40 is rotated by the hinge device 35, the first frame 10 connected to the hip joint 40 may be pivoted around the x axis.

A slide 36 may be provided in a back surface of the hinge device 35, and a rail 37 may be provided in the waist fixing device 30. The rail 37 may extend in the x axis direction. The x-axis direction may be a direction of the user's waist circumference. According to the user's motion, the slide 36 may slide along the rail 37. The slide 35 may pivot the first frame 10 and the hip joint 40 connected to the hinge device 35 around a z axis by sliding the slide 36 along the rail 37.

In this manner, the first frame 10 may be pivoted with three degrees of freedom (DOF) by the hip joint 40, the hinge device 35, and the rail 37.

While an operation of pivoting around the hip joint 40 with one degree of freedom (DOF) using the first wire 31 may require the power source, the other operations with two degrees of freedom (DOF) may be performed according to the user's movement without power from the power source.

The second frame 20 may be pivoted with respect to the first frame 10 with at least one degree of freedom (DOF). The second frame 20 pivotably connected to the first frame 10 by the knee joint 50 may be pivoted by shortening or extending a second wire 32. The second wire 32 may be wrapped around a pulley 34 connected to the driving source, and the second wire 32 may be connected to the second frame 20 through the knee joint 50.

For example, when the driving source rotates the pulley 34 to wrap the second wire 32 around the pulley 34, the second frame 20 may be pivoted around the y axis in a first direction. When the driving source rotates the pulley 34 to release the second wire 32 from the pulley 34, the second frame 20 may be pivoted around the y axis in a second direction opposite to the first direction.

The foot structure 70 may be pivoted with respect to the second frame 20 with three degrees of freedom (DOFs). The foot structure 70 and the second frame 20 may be pivotably connected by the ankle joint 60. The foot structure 70 or the second frame 20 may be pivoted around the ankle joint 60 according to the user's movement without power from the power source.

A first holder 80 may be connected to the first frame 10. The first holder 80 may be configured to wrap around the user's femoral region such that the first holder 80 may mount the first frame 10 on the user's femoral region. The first holder 80 may include a plurality of connected first links 82. For example, the first holder 80 may be formed by connecting the plurality of first links 82.

A second holder 90 may be connected to the second frame 20. The second holder 90 may be configured to wrap around the user's calf such that the second holder 90 may mount the second frame 20 on the user's calf. The second holder 90 may include a plurality of connected second links 92. For example, the second holder 90 may be formed by connecting the plurality of second links 92.

At least one of the first frame 10 and the second frame 20 may be attached to the user's body by pivotably connecting the plurality of links 82, 92 thereabout. Accordingly, the first frame 10 and/or the second frame 20 may come in close contact with the user's body. For example, when the first frame 10 is attached by pivotably connecting the plurality of first links 82, the plurality of first links 82 may pivot in an appropriate angle and come in close contact with the femoral region according to a curvature of the femoral region with which the first frame 10 comes in contact.

The plurality of frame links forming the first frame 10 or the second frame 20 may include first combining units and the second combining units.

The first combining unit may include a protrusion from a first side of the links and the second combining unit may include protrusion from a second side of the links facing the first side of the links. The first combining units may be pivotably connected the second combining units by pins.

A guide unit configured to guide two pins inserted thereinto may be formed in the first combining unit. The guide unit may include a first guide unit and a second guide unit. The first guide unit may be provided in the form of a curve having a bottom point or a peak point. The second guide unit may be provided in the form of a straight line in a vertical direction. The two pins may be inserted into the first guide unit or the second guide unit such that the pins are guided, and may be supported by an inner side wall of the first guide unit or an inner side wall of the second guide unit. The plurality of frame links may rotate and move linearly in the vertical direction simultaneously due to the two pins being guided by the guide unit.

The shape of the curve of the first guide unit may be such that even when the plurality of frame links are pivoted, an overall height of the first frame 10 and/or the second frame 20 formed by the plurality of frame links may not be varied. Also, since the pin connecting the frame links is supported by the inner side wall of the guide unit, buckling may be prevented even when the plurality of frame links are pivoted.

Figure 4:
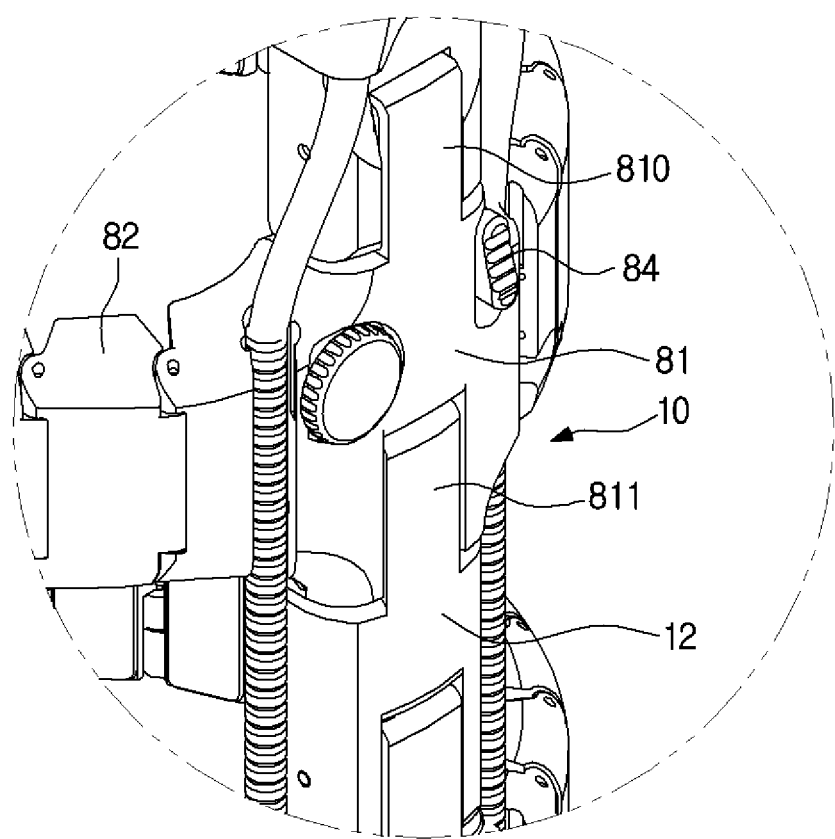
FIGS. 4 and 5 are diagrams illustrating a part of the walking assistant robot illustrated in FIG. 3.
Figure 5:
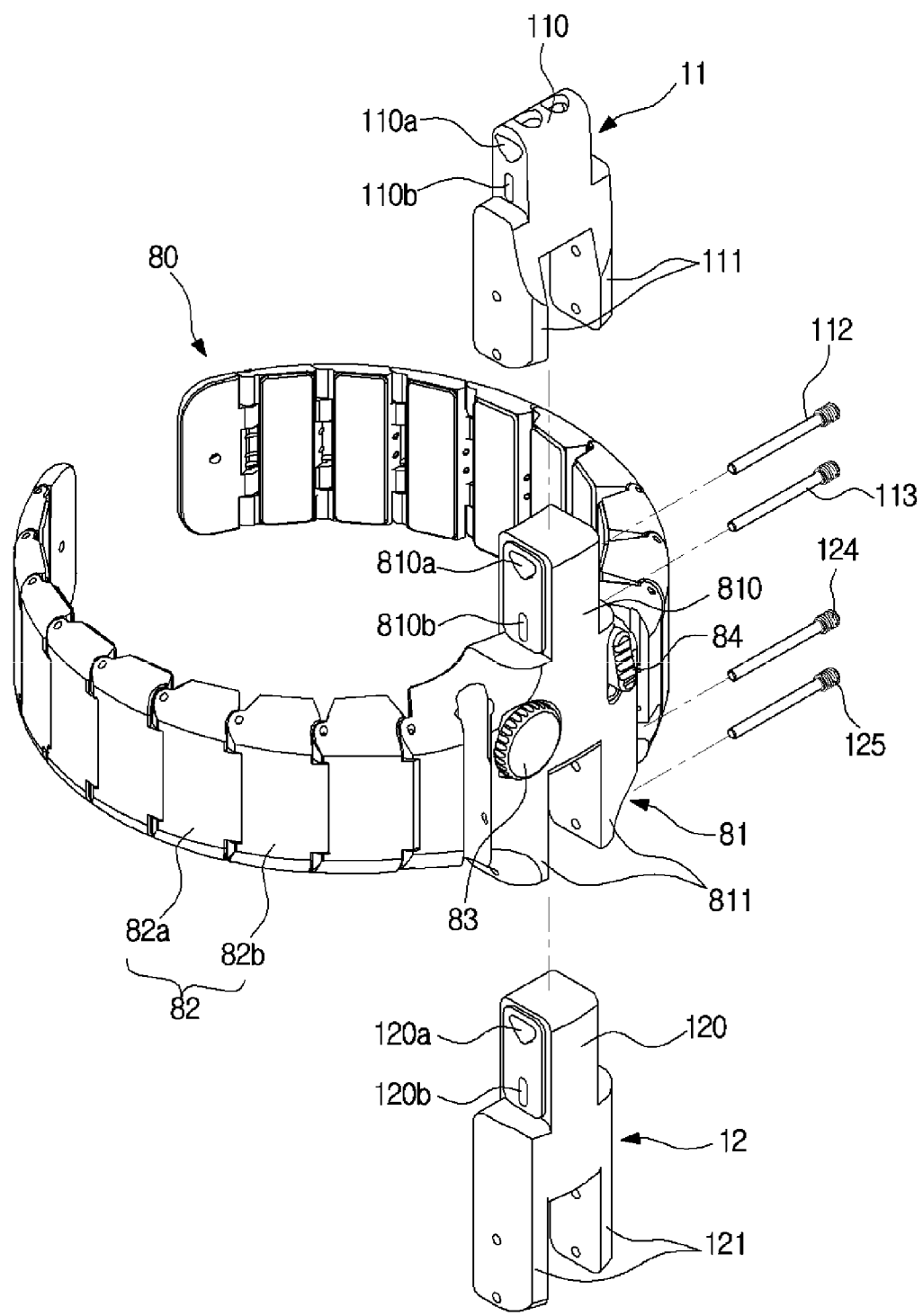

FIGS. 4 and 5 are diagrams illustrating a part of the walking assistant robot illustrated in FIG. 3.

As illustrated in FIGS. 3 to 5, the first and second holders 80 and 90 of the walking assistant robot 1 according to some example embodiments may be connected to the first and second frames 10 and 20, respectively.

Hereinafter, the first holder 80 connected to the first frame 10 will be described. The second holder 90 connected to the second frame 20 may be provided similar to the first holder 80. Therefore, for the sake of brevity repeated description thereof will be omitted.

The first holder 80 includes a holder main body 81 and the plurality of first links 82 connected to the holder main body 81. The holder main body 81 may form a part of the frame 10 to which the first holder 80 is connected.

The plurality of first links 82 may be connected perpendicular to the frame 10. When the frame 10 extends along the user's leg in the vertical direction, the plurality of first links 82 may be connected perpendicular to the frame 10 so as to wrap around the user's leg.

The first frame 10 may include the first frame link 11 and the second frame link 12. The holder main body 81 may be disposed between the first frame link 11 and the second frame link 12 such that the holder main body 81 may be one of the plurality of frame links forming a part of the first frame 10. The holder main body 81 is pivotably connected to the first frame 10 and pivoted in an appropriate angle according to the curvature of the femoral region with which the first frame 10 comes in contact, and thereby the first frame 10 may come in relatively close contact with the femoral region.

With regard to the holder main body 81 disposed on the first frame 10 between the first frame link 11 and the second frame link 12, the holder main body 81 may include a first combining unit 810 and a second combining unit 811 provided in a position facing the first combining unit 810. The first combining unit 810 may be formed to protrude from one side of the holder main body 81. The second combining unit 811 may be formed to protrude from the other side of the holder main body 81.

Similar to the first holder 80 of the first frame 10, the first frame link 11 and the second frame link 12 attached thereto may also include combining units. For example, the first frame link 11 may have a first combining unit 110 protruding from one side of the first frame link 11, and a second combining unit 111 may protrude from the other side thereof. Likewise, the second frame link 12 may have a first combining unit 120 protruding from one side of the second frame link 12, and a second combining unit 121 may protrude from the other side thereof.

As illustrated in FIG. 5, the first combining unit 810 protruding from one side of the holder main body 81 may be pivotably connected by the second combining unit 111 of the first frame link 11 via pins 112 and 113. Likewise, the second combining unit 811 protruding from the other side of the holder main body 81 may be pivotably connected by the first combining unit 120 of the second frame link 12 via pins 124 and 125.

With regard to the first frame link 11 of the first frame 10, the holder main body 81 may perform rotational motion with respect to the first frame link 11 and linear motion in the vertical direction. In this case, the pins 112 and 113 penetrating the holder main body 81 and the first frame link 11 may be guided by guide units 810a and 810b formed in the first combining unit 810 of the holder main body 81. The guide units 810a and 810b may include the first guide unit 810a in the form of a curve having a bottom point and/or a peak point and the second guide unit 810b in the form of a straight line extending in the vertical direction. The pins 112 and 113 may be guided by being inserted into the first guide unit 810a and the second guide unit 810b, respectively.

Similar to the first frame link 11 of the first frame 10, with regard to the second frame link 11 of the first frame 10, the holder main body 81 may perform rotational motion with respect to the second frame link 12 and linear motion in the vertical direction. In this case, the pins 124 and 125 penetrating the holder main body 81 and the second frame link 12 may be guided by guide units 120a and 120b formed in the first combining unit 120 of the second frame link 12. The guide units 120a and 120b may include the first guide unit 120a in the form of a curve having a bottom point or a peak point, and the second guide unit 120b in the form of a straight line extending in the vertical direction. The pins 124 and 125 may be guided by being inserted into the first guide unit 120a and the second guide unit 120b, respectively.

In the first combining unit 110 of the first frame link 11, a first guide unit 110a in the form of a curve having a bottom point or a peak point, and a second guide unit 110b in the form of a straight line extending in the vertical direction may be formed.

An additional second combining unit of another frame link (not shown) may be provided adjacent to the first frame link 11 and located thereabove, and the pins penetrating the first guide unit 110a or the second guide unit 110b, the first frame link 11 may perform rotational motion with respect to another link that is adjacent to the first frame link 11 and located thereabove and linear motion in the vertical direction.

The first and second combining units 110 and 111, 810, 811 may have a shape of one of a projecting tongue and a corresponding grove and the guide units 110a, 110b, 120a, 120b, 810a and 810b may be traversing bores having the aforementioned shapes such that the tongues and groves are pivotably connected via pins inserted into the transverse bore provided through the tongue and groove of adjacent first and second combining units 110 and 111, 810, 811.

Similar to the first frame link 11, the second frame link 12 may perform rotational motion and linear motion in the vertical direction by the second combining unit 121 of the second frame link 12, and pins penetrating the first guide unit in the form of a curve having a peak point and a bottom point formed in the first combining unit or the second guide unit in the form of a straight line extending in the vertical direction of another frame link that is adjacent to the second frame link 12 and located therebelow.

Figure 6:
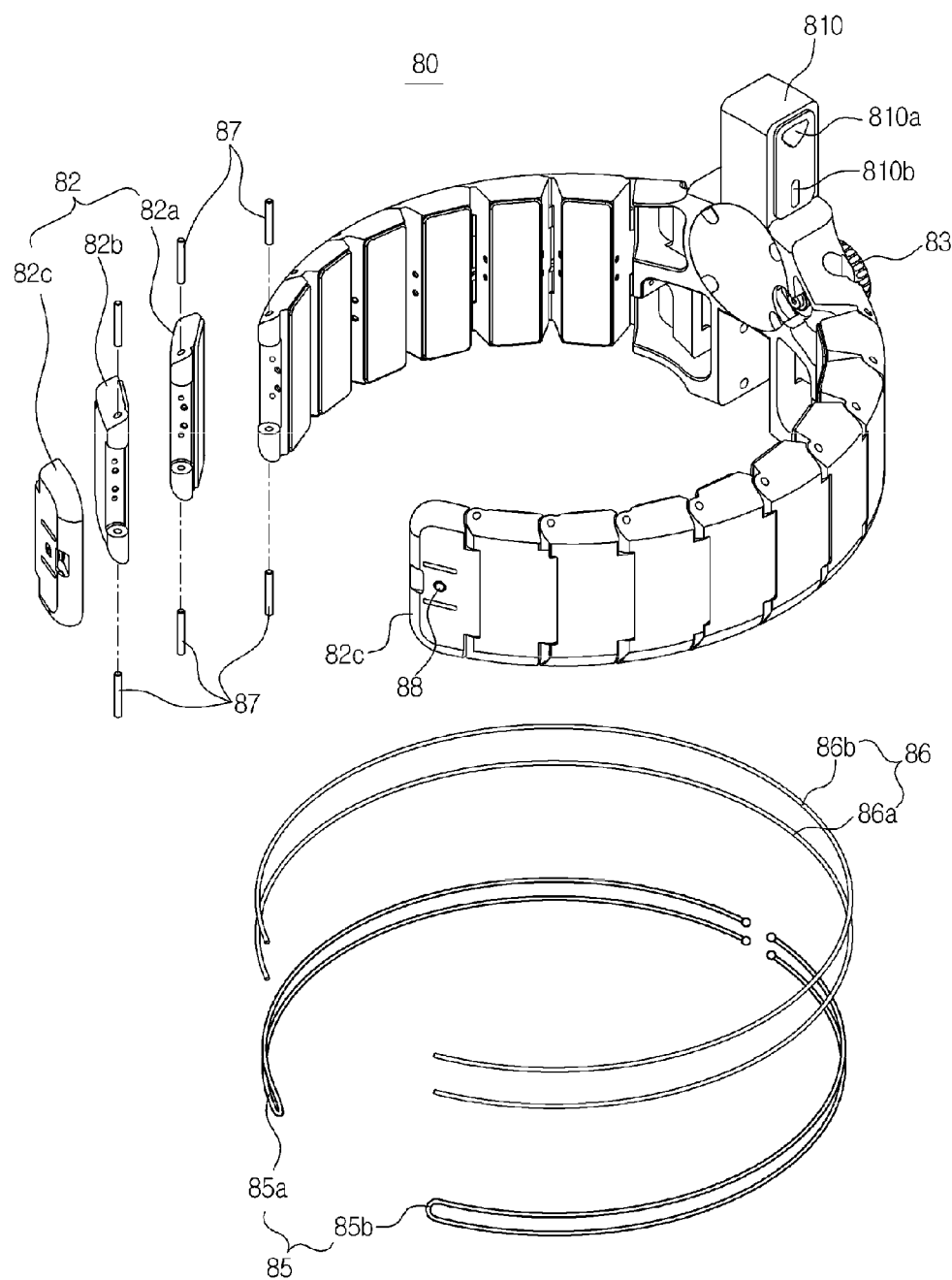
FIG. 6 is an exploded perspective view of a holder included in the walking assistant robot according to some example embodiments.
Figure 7:
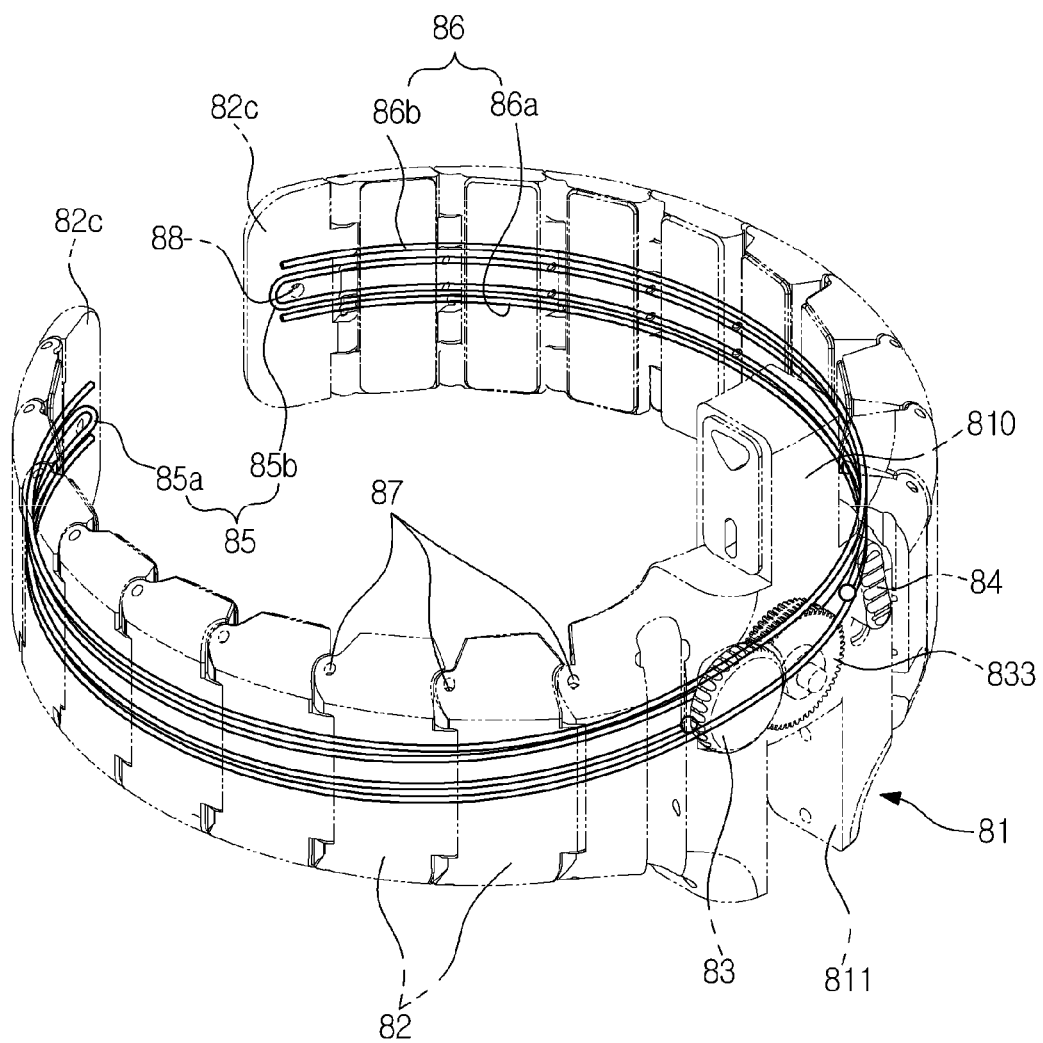
FIG. 7 is a diagram illustrating a wire disposed in the walking assistant robot according to some example embodiments.
Figure 8:
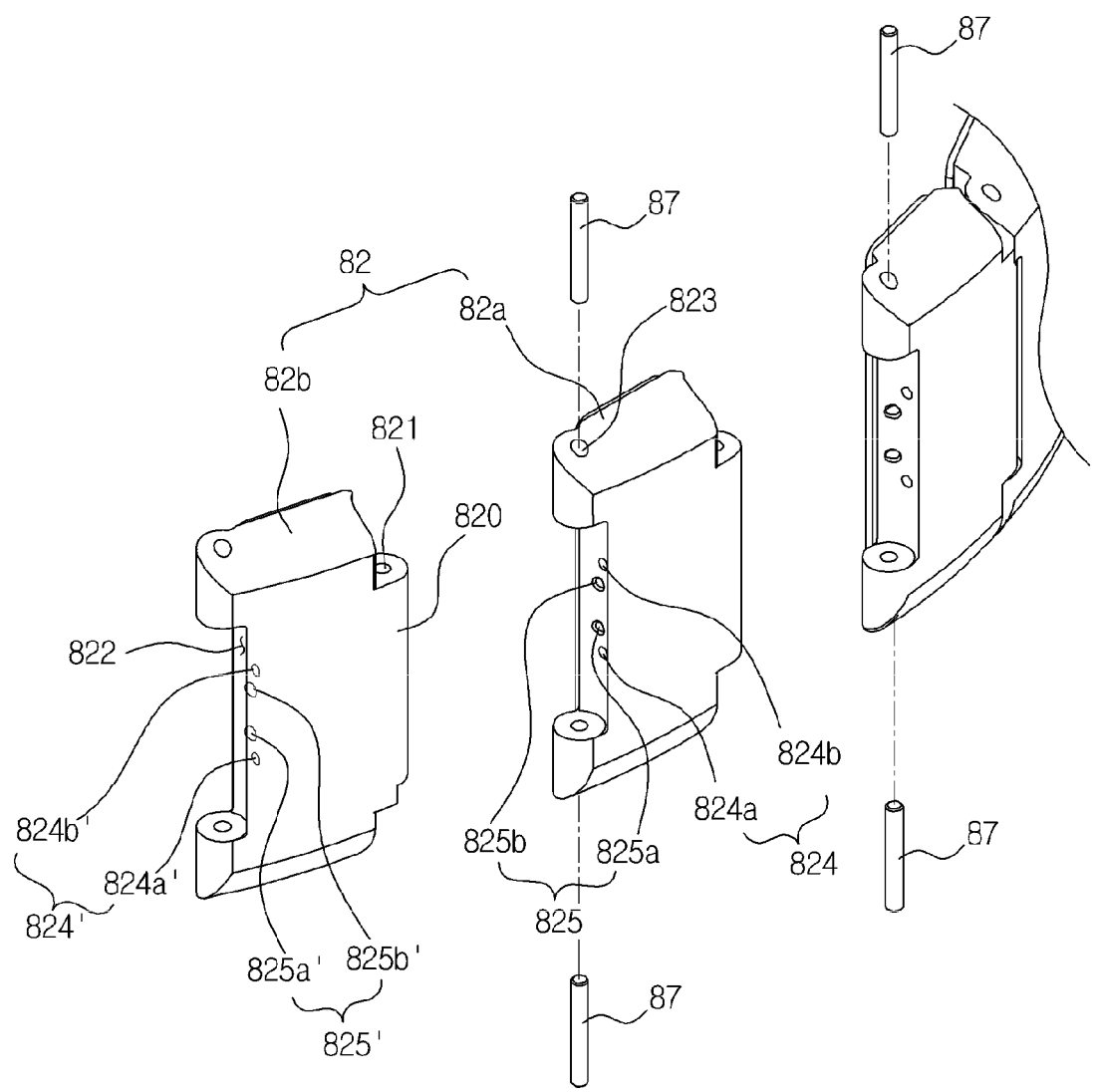
FIG. 8 is a diagram illustrating links forming the holder according to some example embodiments.
Figure 9:
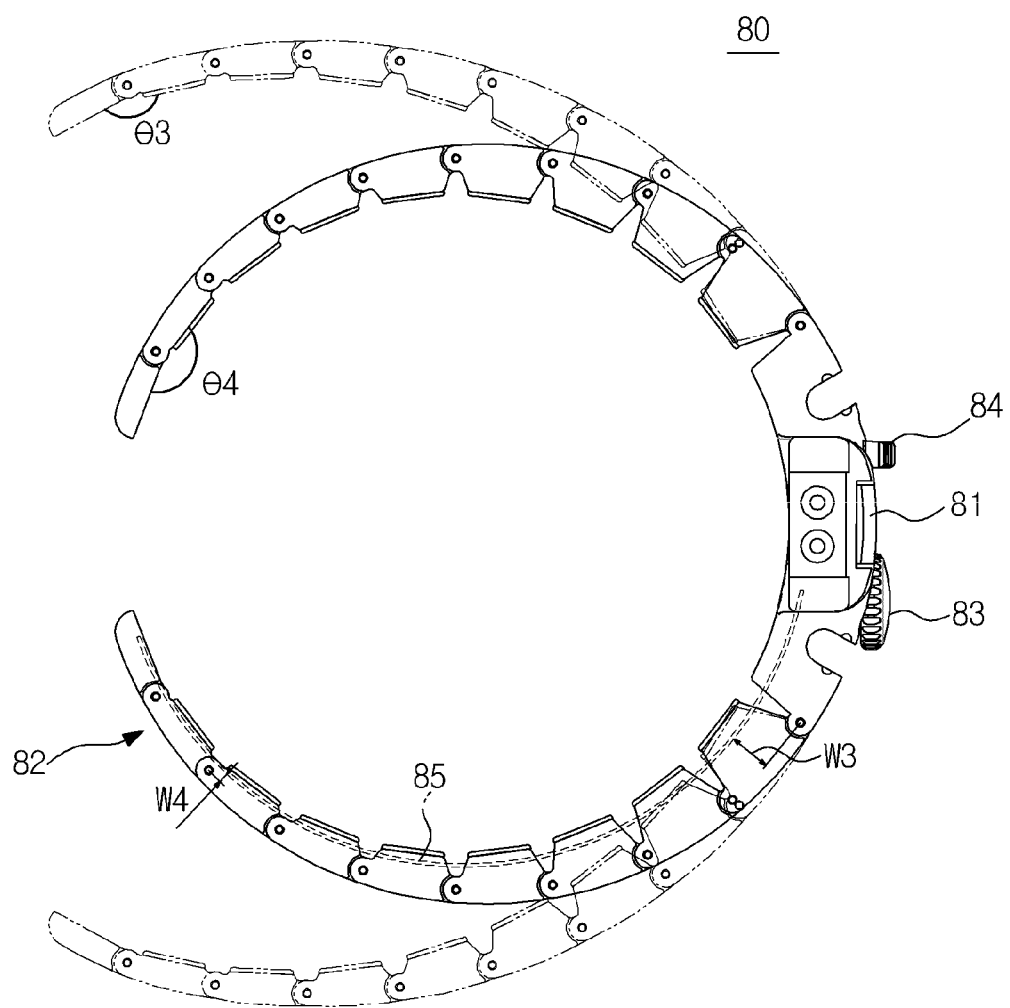
FIG. 9 is a diagram illustrating an operation of the holder according to some example embodiments.

FIG. 6 is an exploded perspective view of a holder included in the walking assistant robot according to some example embodiments. FIG. 7 is a diagram illustrating a wire disposed in the walking assistant robot according to some example embodiments. FIG. 8 is a diagram illustrating links forming the holder according to some example embodiments. FIG. 9 is a diagram illustrating an operation of the holder according to some example embodiments.

As illustrated in FIGS. 6 to 9, the walking assistant robot 1 according to some example embodiments may include the first holder 80 may facilitate mounting of the walking assistant robot 1 on the user's body. The first holder 80 may include the holder main body 81 and the plurality of links 82 connected to the holder main body 81. The plurality of links 82 may be pivotably connected and provided to wrap around the user's body by the user's manipulation.

A combination of the plurality of links 82 may be called a link assembly. The link assembly may be provided in left and right sides of the holder main body 81. A cable 85 (to be described below) may be mounted on the link assembly, and a curvature of the link assembly may be adjusted by tension applied to the cable 85. In other words, the link assembly may be bent by tension applied to the cable 85. For example, as illustrated in FIG. 9, an angle (θ3) formed by inner side surfaces of adjacent links before the tension is applied to the cable 85 may be greater than an angle (θ4) formed by inner side surfaces of adjacent links after the tension is applied to the cable 85.

The link assembly may be bent and the inner side surface may come in close contact with the user's body. The user may adjust the tension applied to the cable 85 to appropriately change a pressure applied by the inner side surface of the link assembly to the user's body. A pad made of a silicone, a rubber, and the like may be attached to the inner side surface of the link assembly with which the user's body comes in contact by the cable 85. Therefore, it is possible to reduce (or, alternatively, eliminate) discomfort generated by frictional force between the inner side surface of the link assembly and the user's body.

When the first holder 80 is mounted to wrap around the user's body, in the inner side surface of the link assembly, force applied to the user's body by the tension caused by the cable 85 may be distributed and transmitted throughout the entire inner side surface of the link assembly with which the user's body comes in contact. By distributing and transmitting the tension caused by the cable 85 to the user's body, to the holder 80 may apply a uniform pressure to the user's body. For example, minimum distances W2 and W3 between a pin 87 included in the link assembly and the cable 85 become shorter from the holder main body 81 side to an end of the link assembly, and force applied by the inner side surface of the link assembly to the user's body is distributed and transmitted to the user's body such that the uniform pressure is applied to the user's body.

Specifically, the minimum distance W2 between the pin 87, which connects between a link located in the holder main body 81 side and a link adjacent thereto, and the cable 85 may be longer than the minimum distance W3 between the pin 87, which connects between a link located in an end side of the link assembly and a link adjacent thereto, and the cable 85. The minimum distance between the cable 85 and the inner side surface of the link assembly may be uniform throughout the entire link assembly.

As discussed above, the first holder 80 may include the cable 85. The cable 85 may penetrate the link assembly. The cable 85 may include a first cable 85a penetrating the link assembly provided in a left side of the holder main body 81 and a second cable 85b penetrating the link assembly provided in a right side of the holder main body 81.

The cable 85 may extend from a link 82c located in the end of the link assembly to the holder main body 81 and pass through the plurality of links 82. When the link assembly is provided in left and right sides of the holder main body 81, the cable 85 may be provided in the link assembly provided in the left side of the holder main body 81 and the link assembly provided in the right side of the holder main body 81. The cable 85 may penetrate a center portion of a side surface of each of the links 82 included in the link assembly.

According to some example embodiments, one side of the cable 85 may be fixed at the link 82c located in the end of the link assembly (e.g., an end link), and the other side of the cable 85 may be fixed at the holder main body 81 side. For example, the other side of the cable 85 may be connected to a manipulating unit 83 side provided at the holder main body 81.

According to other example embodiments, rather than utilize two cables, the cable 85 may be a single cable where one side of the cable 85 is fixed at one side of the holder main body 81, passes through the link assembly, wraps around a fixing pin 88 provided in the link 82c located in the end of the link assembly, passes through the link assembly again, and extends back to the holder main body 81. That is, a single cable 85 may reciprocate and pass through the link assembly twice. The other side of the cable 85 may be connected to the manipulating unit 83 side provided in the holder main body 81.

According to still other example embodiments, a plurality of cables 85 may pass through the link assembly, one side of each cable may be fixed in the end link 82c located in the end of the link assembly, and the other side may be connected to the manipulating unit 83 provided at the holder main body 81. When the cable 85 passes through the link assembly a plurality of times, the link assembly may be stably mounted on or detached from the user's body by the user's manipulation.

The manipulating unit 83 included in the holder main body 81 may be configured to adjust a length of the cable 85. The manipulating unit 83 may be an adjuster configured to adjust an amount of tension provided by the cable. For example, the manipulating unit 83 may be a switch, a dial, etc.

The user may manipulate the manipulating unit 83 to adjust the length of the cable 85 connected to the manipulating unit 83 such that the plurality of links 82 wrap around the user's body and/or are detached from the user's body. The holder 80 is configured such that when the length of the cable is adjusted, the contact force of the link assembly with which the user's body comes in contact also changes.

The first holder 80 may further include a wire 86. The wire 86 may be a spring wire having elasticity. The wire 86 may pass through the link assembly. The wire 86 may pass through all link assemblies provided in the left and right sides of the holder main body 81. The wire 86 may prevent the plurality of links 82 included in the link assembly from being bent sharply at a specific link. For example, even when tension is applied to the cable 85 such that the link assembly restrains the user's body, the wire 86 may prevent excessive bending of a specific link 82.

For example, the wire 86 may pass through an upper and/or a lower portion of the cable 85 with respect to the cable 85 passing through the link assembly. For example, the wire 86 may include a first wire 86a and a second wire 86b. A wire passing through the upper portion of the cable 85 of the link assembly may be the first wire 86a, and a wire passing through the lower portion of the cable 85 of the link assembly may be the second wire 86b.

The plurality of links 82 may be pivotably connected by the pin 87. The plurality of links 82 may include a first link 82a and a second link 82b. Each of the first link 82a and the second link 82b may include a connecting unit 820 formed to protrude from one side and an accommodating unit 822 formed in the other side. The connecting unit 820 formed in the second link 82b may be inserted into an accommodating unit 822 formed in an adjacent first link 82a.

In the connecting unit 820, a pin-through hole 821 into which the pin 87 can be inserted may be formed. In the above or below the accommodating unit 822, a pin-through hole 823 into which the pin 87 can be inserted may be formed so as to penetrate to the accommodating unit 822. The pin-through hole 821 formed in the connecting unit 820 may be provided to correspond to the pin-through hole 823 formed in the accommodating unit 822. The pin 87 passing through the pin-through hole 823 formed in the accommodating unit 822 side formed in the first link 82a may be inserted into the pin-through hole 821 formed in the connecting unit 820 of the second link 82b accommodated in the accommodating unit 822. When the pin 87 passes through the pin-through hole 823 formed in the accommodating unit 822 side of the first link 82a and the pin-through hole 821 formed in the connecting unit 820 side of the second link 82b, the first link 82a and the second link 82b may be pivotably connected with respect to the pin 87.

Like the first and second combining units associated with the frame 10, the connecting units 820 associated with the holder 80 may have a shape of a projecting tongue and the accommodating units 822 associated with the holder 80 may have a shape of a corresponding grove. Likewise, like the guide units associated with the frame 10, the pin-through holes 821, 823 associated with the holder 80 may be traversing bores having the aforementioned shapes such that the tongues and groves are pivotably connected via the pins 87 inserted into the transverse bore provided through the tongue and groove of adjacent connecting units 820 and accommodating units 822.

As illustrated in FIG. 8, in the link assembly, a cable-through hole 825 may be formed in the links 82. The cable-through hole 825 may be configured to accept the cable 85 such that the cable 85 can be inserted therein. The cable-through hole 825 may be formed in a side surface of the link 82. Specifically, the cable-through hole 825 may be formed to penetrate both facing side surfaces of the link 82. The cable-through hole 825 formed in the links 82 forming the link assembly may be formed to communicate with the cable-through hole 825 formed in an another adjacent link. For example, the cable-through hole 825 formed in the first link 82a may communicate with the cable-through hole 825 formed in the second link 82b adjacent to the first link 82a.

When the cable 85 reciprocates and passes through the link assembly twice or more or a plurality of cables 85 pass through the link assembly, the cable-through hole 825 may be formed in a number corresponding to the number of times the cable 85 passes through the link assembly. For example, when the cable 85 reciprocates and passes through the link assembly twice, a first cable-through hole 825a and a second cable-through hole 825b may be formed in each link 82 forming the link assembly. The cable 85 may pass through the first cable-through hole 825a formed in each link 82, pass through the second cable-through hole 825b, and return.

In the end link 82c located in the end of the link assembly, the fixing pin 88 configured to fix a location of the cable 85 may be provided. In the link 82c located in the end of the link assembly, the cable-through hole 825 may be formed in only one side. The cable 85 that has passed through the first cable-through hole 825a formed in the plurality of links 82 is wrapped around the fixing pin 88 and a direction thereof may be changed toward the second cable-through hole 825b. The tension applied to the cable 85 may be transmitted by the fixing pin 88 to the link 82c located in the end of the link assembly.

Fixing of the cable 85 in the holder 80, such that the cable 85 can be shortened or extended, in the holder main body 81 will be described below.

In the link assembly, wire-through holes 824 and 826 into which the wire 86 can be inserted may be provided. The wire-through holes 824 and 826 may be formed in the plurality of links 82 included in the link assembly. The wire-through holes 824 and 826 formed in the link 82 may be formed to communicate with the wire-through holes 824 and 826 formed in a link adjacent thereto.

The wire-through hole 824 may be provided so as to penetrate an inner side wall of the accommodating unit 822 provided in each link 82. Two wire-through holes 824 may be formed. The two wire-through holes 824 may be disposed in the inner side wall of the accommodating unit 822 in the vertical direction.

The wire-through hole 826 provided in the end link 82c provided in the end of the link assembly may be exposed to the outside. When the plurality of links 82 are connected to form the link assembly, the wire may be inserted through the wire-through hole 826 formed in the link 82c provided in the end of the link assembly. The wire 86 inserted through the wire-through hole 826 may pass through the wire-through hole 824 formed in each link 82 of the link assembly. Accordingly, the wire 86 may be installed in the link assembly.

Figure 10:
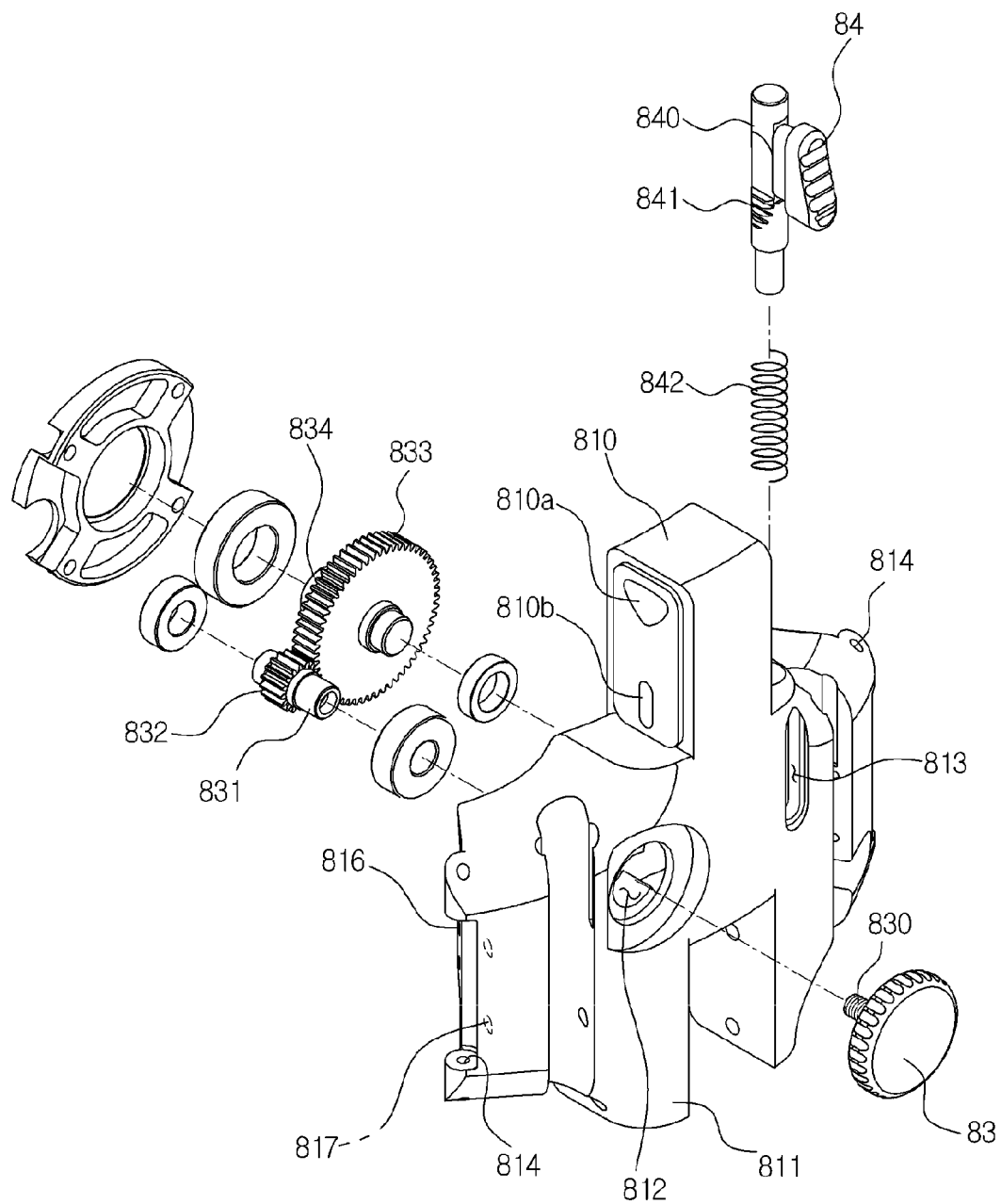
FIG. 10 is an exploded perspective view of a holder main body according to some example embodiments.

FIG. 10 is an exploded perspective view of a holder main body according to some example embodiments.

As illustrated in FIG. 10, the holder main body 81 according to some example embodiments may include the manipulating unit 83 and a locking switch 84. The manipulating unit 83 and the locking switch 84 may be exposed to the outside of the holder main body 81 so as to allow manipulation by the user.

In both side surfaces of the holder main body 81, an accommodating unit 817 or a connecting unit may be provided to connect the link 82. When the accommodating unit 817 is formed in the holder main body 81, a connecting unit of the link 82 adjacent to the holder main body 81 may be accommodated in the accommodating unit 817. The link 82 and the holder main body 81 may be pivotably connected by a pin that penetrates a pin-through hole 814 formed above the accommodating unit 817 and a pin-through hole formed in the connecting unit of the link 82.

Like the first and second combining units associated with the frame 10, the accommodating unit 817 associated with the holder main body 81 may have a shape of a grove configured to pivotably connect to connecting units of a link 82 adjacent to the holder main body 81.

In an inner side of the holder main body 81, a first gear unit 832 may be installed. The first gear unit 832 may be connected to the manipulating unit 83 such that when the user manipulates the manipulating unit 83, the first gear unit 832 may move along with the manipulating unit 83 together.

For example, a coupling unit 830 in which a screw thread is formed in an outer side surface may be provided in the manipulating unit 83. In the first gear unit 832, a coupling boss 831 in which a screw thread is formed in an inner side surface forming a hole may be installed. The coupling unit 830 and the coupling boss 831 may each be one of an external (male) screw thread and a corresponding internal (female) screw thread.

The coupling unit 830 may pass through a first hole 812 formed in the holder main body 81, and coupled to the coupling boss 831 provided in the inner side of the holder main body 81. Accordingly, the manipulating unit 83 and the first gear unit 832 may be connected to move together.

In both side surfaces of the holder main body 81, a cable-through hole 816 through which the cable 85 can pass may be further formed. One end of the cable 85 that has passed through the cable-through hole 816 may be installed in a second gear unit 833 associated with the holder main body 81.

The second gear unit 833 may be configured to mesh with the first gear unit 832. When the first gear unit 832 rotates, the second gear unit 833 may rotate in a direction opposite to a rotation direction of the first gear unit 832. For example, when the first gear unit 832 rotates in a clockwise direction, the second gear unit 833 may rotate in a counterclockwise direction. In the second gear unit 833, a shaft 834 in which at least the end of the cable that passes through the link assembly and the cable-through hole 816 may be connected. The shaft 834 is mounted on the second gear unit 833 and may rotate along with the second gear unit 833.

The end of the cable 85 passing through the link assembly may be fixed in the shaft 834 connected to the second gear unit 833. When the second gear unit 833 rotates in a specific direction, the shaft 834 may rotate along with the second gear unit 833. When the shaft 834 rotates in a specific direction, the cable 85 fixed in the shaft 834 is wrapped around the shaft 834 or the wrapped cable 85 may be released from the shaft 834.

When a single cable 85 is provided to reciprocate the link assembly, one end of the cable 85 may be fixed in the shaft 834, and the other end of the cable 85 may be fixed in one side of the holder main body 81 or one side of the link 82 adjacent to the holder main body 81.

For example, when the user rotates the manipulating unit 83 in a counterclockwise direction, the first gear unit 832 rotates along with the manipulating unit 83 in the counterclockwise direction. When the first gear unit 832 rotates in the counterclockwise direction, the second gear unit 833 may rotate in a clockwise direction. When the second gear unit 833 rotates in the clockwise direction, the cable 85 may be wrapped around the shaft 834. When the cable 85 is wrapped around the shaft 834, the link assembly is bent such that an angle between adjacent links 82 decreases causing the links 82 to come closer to the user's body side, and may restrain the user's body.

When the user rotates the manipulating unit 83 in a clockwise direction, the first gear unit 832 rotates along with the manipulating unit 83 in the clockwise direction. When the first gear unit 832 rotates in the clockwise direction, the second gear unit 833 may rotate in a counterclockwise direction. When the second gear unit 833 rotates in the counterclockwise direction, the cable 85 may be released from the shaft 834. When the cable 85 is released from the shaft, the link assembly may become farther from the user's body by the loosened cable 85 such that an angle between adjacent links increases causing the links 82 to be detached from the user's body.

The holder main body 81 may further include a locking unit (e.g. a brake). The locking unit may include the locking switch 84 and a locking bar 840 connected to the locking switch 84. In one side of the locking bar 840, a locking gear 841 that can be selectively meshed with the second gear unit 833 may be formed.

The locking bar 840 may be provided in the inner side of the holder main body 81. The locking switch 84 may be provided outside the holder main body 81 to be manipulated by the user. The locking switch 84 and the locking bar 840 may be combined to be integrally movable. A second hole 813 is formed in the holder main body 81. The locking switch 84 and the locking bar 840 may be combined through the second hole 813. The second hole 813 may extend in the vertical direction, and the switch 84 may slide in an extending direction of the second hole 813.

An elastic member 842 (e.g., a spring) configured to apply elastic force to the locking bar 840 may be provided below the locking bar 840. The elastic force applied by the elastic member 842 to the locking bar 840 may be exerted upward.

In the locking bar 840, the locking gear 841 that is selectively meshed with the second gear unit 833 may be provided. The locking gear 841 may be provided in a bottom surface of the locking bar 840.

Hereinafter, a structure in which an operation of the manipulating unit 83 is restrained or released by the locking unit will be described.

Figure 11:
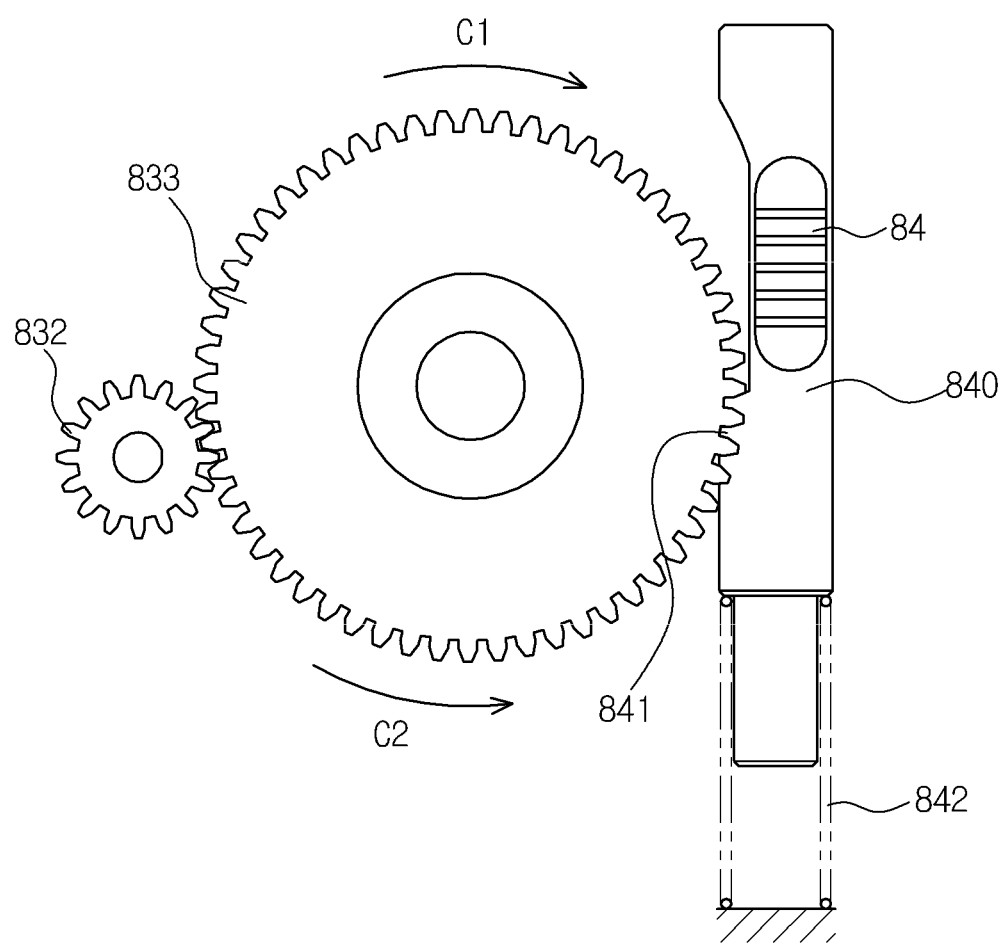
FIG. 11 is a diagram illustrating a state in which a second gear unit is locked according to some example embodiments.
Figure 12:
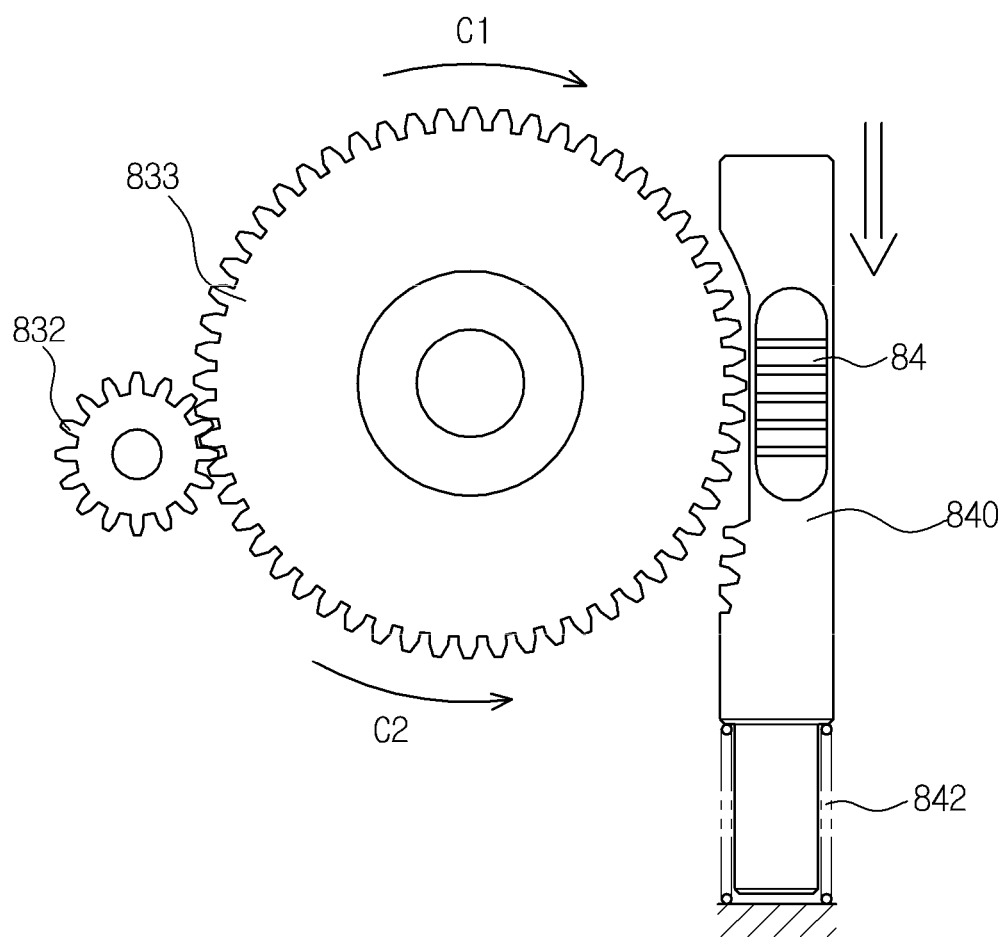
FIG. 12 is a diagram illustrating a state in which locking of the second gear unit is released according to some example embodiments.

FIG. 11 is a diagram illustrating a state in which a second gear unit is locked according to some example embodiments. FIG. 12 is a diagram illustrating a state in which locking of the second gear unit is released according to some example embodiments.

As illustrated in FIGS. 11 and 12, the locking bar 840 may include the locking gear 841 that is selectively meshed with the second gear unit 833. While there is no external force, the locking bar 840 is pushed up due to the elastic member 842, and the locking gear 841 and the second gear unit 833 are meshed with.

As illustrated in FIG. 11, while the second gear unit 833 and teeth of the locking gear 841 are meshed with, the second gear unit 833 may rotate in a clockwise direction c1. When the second gear unit 833 rotates in the clockwise direction c1, the teeth of second gear unit 833 pass sequentially the locking gear 841. While a sawtooth provided in the second gear unit 833 passes through a sawtooth provided in the locking gear 841 sequentially, the locking bar 840 may be pushed down. When a sawtooth provided in the second gear unit 833 passes through a sawtooth provided in the locking gear 841, the locking bar 840 may return upward due to the elastic member 842 provided therebelow. While the second gear unit 833 rotates and pushes down the locking bar 840, the locking bar 840 may repeat an operation of returning upward due to the elastic member 842.

In this manner, since the second gear unit 833 is rotatable in the clockwise direction c1, the user rotates the manipulating unit 83 in a counterclockwise direction to wrap the cable 85 around the shaft 834 such that the link assembly restrains and wraps around the user's body. Accordingly, the first holder 80 may be mounted on the user's body.

While the second gear unit 833 and the locking gear 841 are meshed together, the second gear unit 833 may not rotate in a counterclockwise direction c2. While there is no external force, an upper surface and a side surface of the locking bar 840 are disposed adjacent to the inner side wall of the holder main body 81 and are provided such that there is no space in which the locking bar 840 moves up or to a side.

When the second gear unit 833 tries to rotate in the counterclockwise direction c2, since there is no space in which the locking bar 840 moves up or to a side, the sawtooth provided in the second gear unit 833 does not pass through the sawtooth provided in the locking gear 841, and the second gear unit 833 is interfered with the locking gear 841 and does not rotate. Therefore, even when the user rotates the manipulating unit 83 in a clockwise direction, since the second gear unit 833 may not rotate in the counterclockwise direction c2, it remains in a locking state in which the cable 85 wrapped around the shaft 834 may not be released.

Accordingly, when the user mounts the holder 80 such that the link assembly applies an appropriate pressure to the body, the cable 85 may be fixed so as not to be released from the shaft 834, as long as there is no manipulation of the locking unit. Accordingly, the first holder 80 may be stably mounted on the user's body such that even when a pressure is applied to the first holder 80 while the user walks, the first holder 80 may not be loosened or detached from the user's body.

As illustrated in FIG. 12, when the user applies force greater than the elastic force of the elastic member 842 to move the locking switch 84 down, the locking bar 840 moves downward, and the second gear unit 833 and the locking gear 841 may be separated.

Since the second gear unit 833 is not interfered with the locking gear 841, the second gear unit 833 may rotate in the clockwise direction c1 and the counterclockwise direction c2. While the locking switch 84 is moved down, the user may rotate the manipulating unit 83 in the clockwise direction. When the manipulating unit 83 rotates in the clockwise direction, the second gear unit 833 rotates in the counterclockwise direction c2, and the cable 85 wrapped around the shaft 834 may be released from the shaft 834. When the cable 85 is released from the shaft 834, the length of the cable 85 increases and the link assembly may be separated from the user's body. Accordingly, the first holder 80 may be detached from the body.

When the force applied to the locking switch 84 is released, the locking bar 840 moves upward by the elastic force of the elastic member 842, and the locking gear 841 and the second gear unit 833 may be meshed with again as illustrated in FIG. 10.

Figure 13:
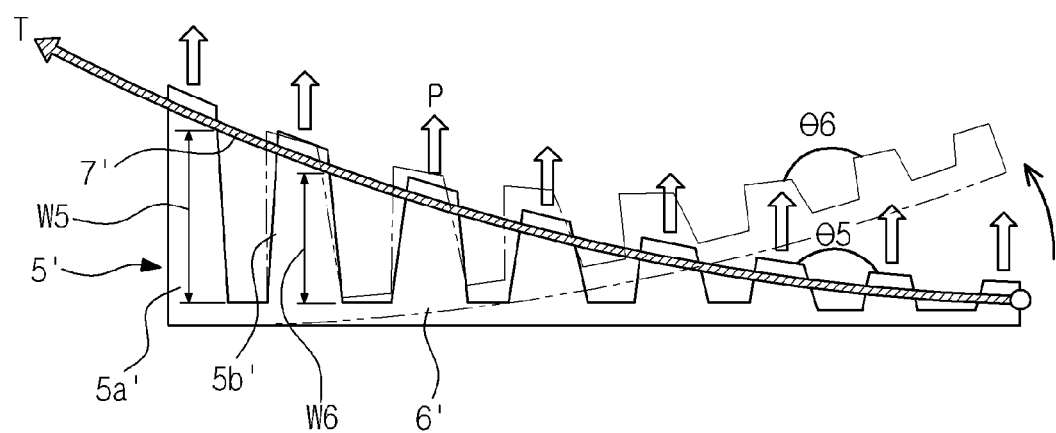
FIG. 13 is a conceptual diagram according to other example embodiments.

FIG. 13 is a conceptual diagram illustrating other example embodiments.

As illustrated in FIG. 13, in other example embodiments, a holder 5' can be mounted on a specific portion of the body. The holder 5' may be provided with a plurality of links connected by a panel 6' having elasticity. The plurality of links connected by the panel 6' may be called a link assembly.

The holder 5' may include a cable 7'. The cable 7' may pass through the plurality of links. In the holder 5', the plurality of links may wrap around the body by tension applied to the cable 7'. One end of the cable 7' may be fixed in a link provided in an end of the holder 5'. Through the other end of the cable 7', tension may be applied to the cable 7'. When the tension is applied to the cable 7', the plurality of links may be pulled by the cable 7' to wrap around the body. An angle ($\theta 5$) formed by inner side surfaces of adjacent links before the tension is applied to the cable 7' may be greater than an angle ($\theta 6$) formed by inner side surfaces of adjacent links after the tension is applied to the cable 7'.

For example, the plurality of links forming the holder 5' may include a first link 5a' and a second link 5b'. The first link 5a' and the second link 5b' adjacent to the first link 5a' may be connected by the panel 6' having elasticity. The cable 7' may pass through the first link 5a' and the second link 5b'. One end of the cable 7' may be fixed in one side of the link assembly. When the other end of the cable 7' is pulled, tension T is applied to the cable 7'. By the tension T applied to the cable 7', the link assembly including the first link 5a' and the second link 5b' may receive driving force to wrap around the user's body.

When the link assembly is pulled by the cable 7' to wrap around the user's body, the inner side surface of each link may press the user's body. In this case, force applied by the inner side surface of each link to the user's body may be distributed. The inner side surface of each link may transmit a uniform pressure P to the user's body. Accordingly, even when the holder 5' is mounted on the user's body, the holder 5' may reduce (or, alternatively, eliminate) discomfort due to transmission of a non-uniform pressure.

A minimum distance between the panel 6' mounted on the link and the cable 7' may decrease from the other side to one side of the cable 7'. Specifically, a minimum distance W5 between the panel 6' connected to the link 5a' located in the other side of the cable 7' and the cable 7' may be greater than a minimum distance W6 between the panel 6' connected to the link 5b' located in one side of the cable 7' and the cable 7'. Accordingly, moment of the panel 6' due to force exerted on the user's body by the inner side surface of each link and moment of the panel 6' due to tension of the cable 7' may be balanced.

Figure 14:
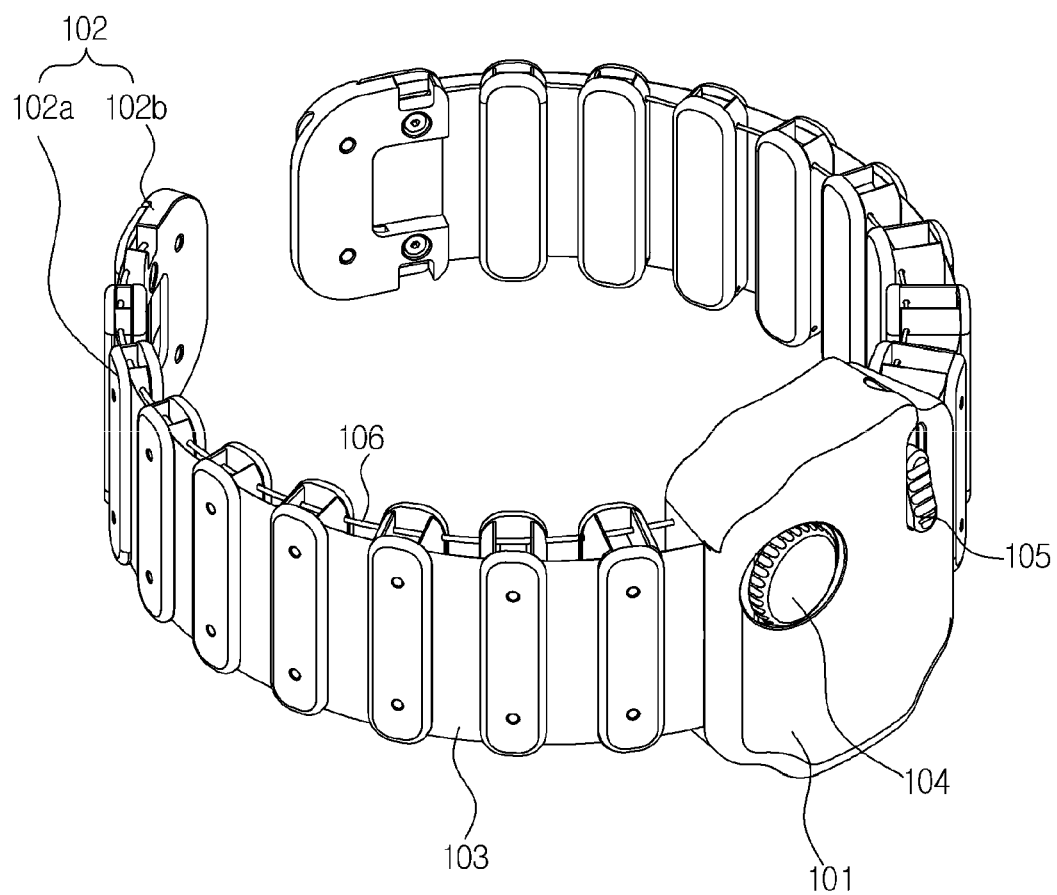
FIG. 14 is a diagram illustrating a holder according to other example embodiments.
Figure 15:
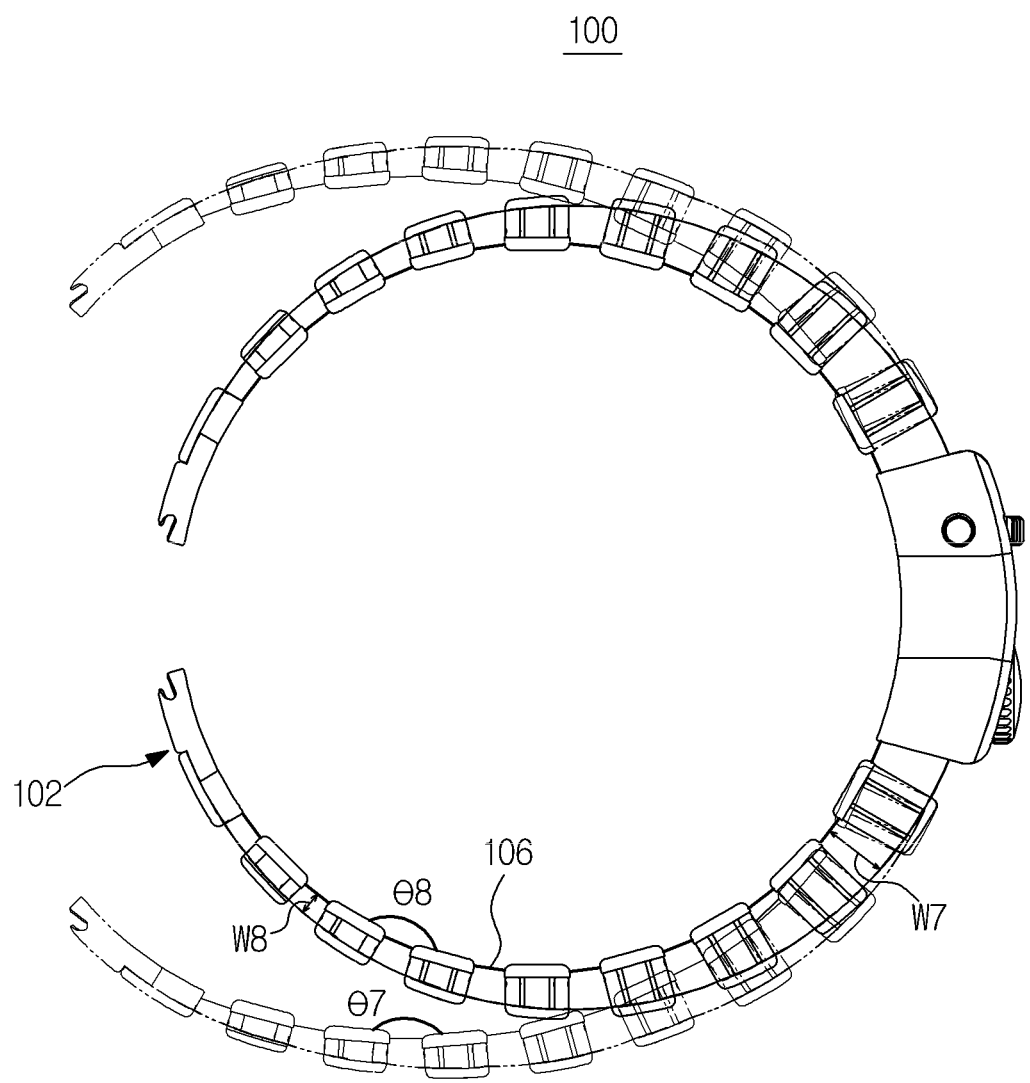
FIG. 15 is a diagram illustrating a link and a cable according to other example embodiments.
Figure 16:
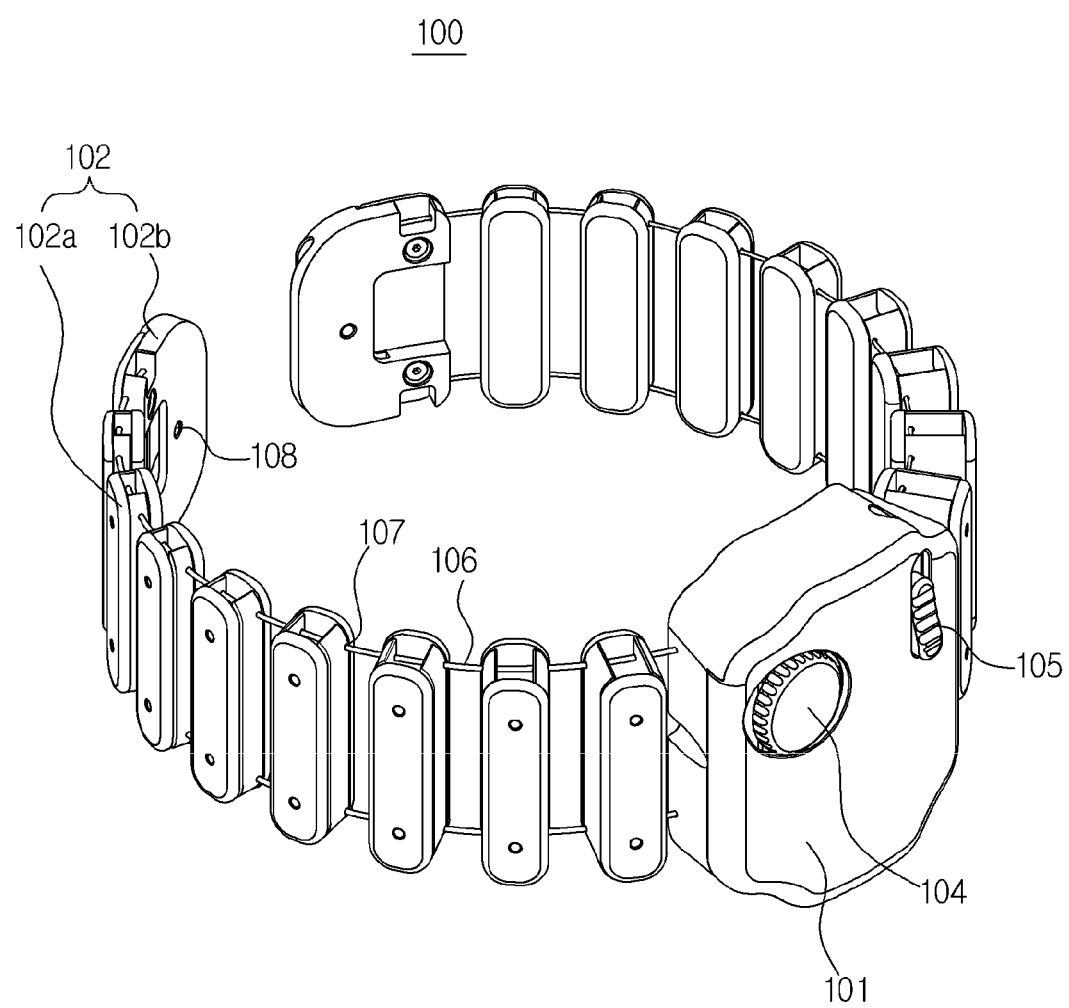
FIG. 16 is a diagram illustrating an operation of a holder according to other example embodiments.

FIG. 14 is a diagram illustrating a holder according to other example embodiments. FIG. 15 is a diagram illustrating a link and a cable of the holder according to other example embodiments. FIG. 16 is a diagram illustrating an operation of the holder according to other example embodiments.

As illustrated in FIGS. 14 and 15, a holder 100 may include a holder main body 101 and a plurality of links 102. The plurality of links 102 may be connected by a panel 103 having elasticity.

In some example embodiments, the panel 103 may serve as the wire 86 and the pin 87 connecting the link 82 in the holder 80. That is, the panel 103 connects the plurality of links 102, and even when tension is applied to a cable 106 (to be described below), the plurality of links 102 may maintain a shape of the link assembly.

A combination of the plurality of links 102 and the panel 103 may be called a link assembly. The link assembly may be connected to the holder main body 101. The link assembly may be connected to left and right sides of the holder main body 101. A pad made of silicone, rubber, and/or the like may be mounted on the inner side surface of the link assembly with which the user's body comes in contact, thereby improving wearability of the user.

The link assembly may include the cable 106 passing through the plurality of links 102. The cable 106 penetrates the plurality of links 102. The cable 106 may pass through the plurality of links 102 a plurality of times. For example, a single cable 106 may reciprocate and pass through the link assembly twice.

A curvature of the link assembly may be adjusted by tension applied to the cable 106. An angle (θ7) formed by inner side surfaces of adjacent links before the tension is applied to the cable 106 may be greater than an angle (θ8) formed by inner side surfaces of adjacent links after the tension is applied to the cable 106.

A minimum distance between the cable 106 and the inner side surface of the link may be the same as in the entire link assembly. When the tension is applied to the cable 106 and the holder 100 is mounted on the user's body, force exerted on the user's body by the link assembly with which the user's body comes in contact is distributed and a uniform pressure may be applied to the user's body throughout an entire contacting area.

For example, a minimum distance W7 between the panel 103 located in the holder main body 101 side and the cable 106 may be greater than a minimum distance W8 between the panel 103 located in the end of the link assembly and the cable 106. In this manner, force due to the tension of the cable 106 may be distributed and transmitted such that each surface of the plurality of links wrapping around the user's body applies a uniform pressure to the user's body.

A fixing pin 108 is provided in a link 102b located in the end of the link assembly. The cable 106 extending from the holder main body 101 may pass through the link assembly, turn around the fixing pin 108, pass through the link assembly again, and extend in the holder main body 101 side.

One side of the cable 106 may be fixed in the holder main body 101 or in a link 102a adjacent to the holder main body 101. The other side of the cable 106 may be fixed in a shaft provided in the holder main body 101.

The holder main body 101 may include a manipulating unit 104 that can be manipulated by the user to decrease or increase a length of the cable 106. The holder main body 101 includes a locking unit configured to lock a shaft side in which the cable 106 is wrapped around such that the cable 106 is selectively extended. The holder main body 101 may include a locking switch 105 capable of manipulating the locking unit.

Since extending or shortening of the cable 106 by the manipulating unit 104, a configuration of the locking unit, and a configuration and an operation of the holder main body 101 related to functions may be similar to those described above with reference to FIGS. 10 to 12 description thereof will not be repeated.

Figure 17:
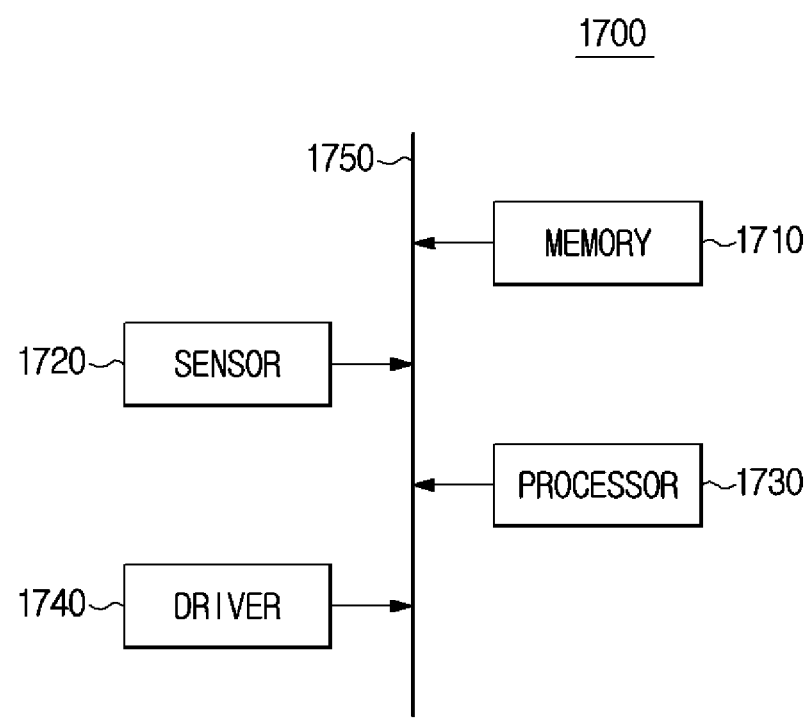
FIG. 17 illustrates a tension device according to some example embodiments.

FIG. 17 illustrates a tension device according to some example embodiments.

As illustrated in FIG. 17, a tension device 1700 may include, for example, a memory 1710, a sensor 1720, a processor 1730, and a driver 1740 that may send data to and/or receive data from one another using a data bus 1750.

The memory 1710 may be any device capable of storing data. For example, the memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The sensor 1720 may be configured to sense whether the user is walking. For example, the sensor 1720 may be a pressure sensor. The pressure sensor may be a ground reaction force (GRF) sensor that senses GRF transferred to the user's foot when the user walks.

The processor 1730 may be any device capable of processing data including, for example, a microprocessor configured to carry out specific operations by performing arithmetical, logical, and input/output operations based on input data, or capable of executing instructions included in computer readable code. The processor 940 may be a logic chip, for example, a central processing unit (CPU), a controller, or an application-specific integrated circuit (ASIC), that when, executing the instructions stored in the memory 1710, configures the processor 1730 as a special purpose machine such that the processor 1730 is configured to determine an amount of tension to apply to the cables associated with the holder. The processor 1730 may determine the amount of tension to apply to the cables based on a result of sensing performed by the sensor 1720.

The driver 1740 may be a motor that generates torque according to electric energy supplied from a power supply (not shown). The motor may be provided with an encoder. Alternatively, the driver 1740 may include at least one piston or cylinder device that is operated by electric energy or by fluidic pressure such as, for example, hydraulic pressure or pneumatic pressure generating torque. The driver 1740 may exert an amount of torque on the cables based on instructions received from the processor 1730.

In some example embodiments, the holder may include a bladder and an air pressure generator (not shown), the processor 1730 may vary an amount of pressure applied to the legs of the user by instructing the air pressure generator to inflate and/or deflate the bladder. An amount of inflation may depend on, for example, the result of sensing performed by the sensor 1720.

In this manner, the plurality of links are pivotably connected, and the holder may be mounted on or detached from the user's body by shortening or extending the cable. Since a degree of pressing by the link assembly is adjusted to match a size of the user's body by extending or shortening the cable, the holder may reduce (or, alternatively, eliminate) wearing discomfort due to a different size of the body on which the holder is mounted. Also, a distance between a cable of the link assembly and a pivot unit is adjusted to distribute and transmit force exerted on the user's body by the plurality of links due to the tension of the cable. Force exerted on the user's body by the plurality of links is distributed and transmitted, and a size of the pressure applied to the user's body by the inner side surface of the link assembly with which the user's body comes in contact is equalized, thereby eliminating the user's discomfort due to a non-uniform pressure while mounting the holder.

According to some example embodiments, a holder may be more easily mounted on a user's body by applying tension to a cable. In an inner side surface of the holder with which the user's body comes in contact, a contact surface with the holder may not be uncomfortable to the user.

Although a few example embodiments have been shown and described, it would be appreciated by those skilled in the art that changes may be made in these example embodiments without departing from the principles and spirit thereof, the scope of which is defined in the claims and their equivalents.

What is claimed is:

1. A holder configured to mount on a user, the holder comprising:
    a link assembly including a plurality of interconnected links configured to wrap around a body part of the user, the plurality of interconnected links having an inner side surface facing the body part and an outer side surface facing a direction opposite the inner side surface, the plurality of interconnected links being pivotably connected by pins at the outer side surface;
    a cable configured to traverse the plurality of interconnected links in the link assembly, and to adjust an angle between adjacent ones of the plurality of interconnected links in response to tension applied thereto; and
    a holder main body configured to have a first side of the cable mounted thereto, wherein the inner side surface of each of the plurality of interconnected links is a same first distance from the cable while a second distance between the outer side surface of each of the plurality of interconnected links and the cable gradually decreases from a first link of the plurality of interconnected links connected to the holder main body to an end link of the plurality of interconnected links.

2. The holder according to claim 1, wherein the holder main body includes an adjuster configured to adjust an amount of tension applied to the cable.

3. The holder according to claim 2, wherein the adjuster is configured to shorten the cable such that the amount of tension applied to the cable increases and an angle between adjacent links decreases.

4. The holder according to claim 1, wherein
    the plurality of interconnected links include a first group of interconnected links and a second group of interconnected links, each of the first and second group of interconnected links having a first end link connected to the holder main body and a second end link at an opposite end of a respective one of the first and second group of interconnected links from the first end link.

5. The holder according to claim 2, wherein
    the first side of the cable is attached to a gear shaft associated with the holder main body, and
    the gear shaft is configured to connect to a gear.

6. The holder according to claim 5, wherein
    the gear is configured to rotate in response to a driving force from the adjuster, and
    the gear shaft is configured to shorten or extend the cable in response to a rotation of the gear.

7. The holder according to claim 6, wherein the holder main body further includes a brake configured to selectively impede the rotation of the gear connected to the gear shaft.

8. The holder according to claim 7, wherein the brake includes a locking gear that is selectively meshed with the gear.

9. The holder according to claim 8, wherein when the locking gear is meshed with the gear, the locking gear is configured to impede rotation of the gear in a specific direction.

10. The holder according to claim 9, wherein the specific direction is a direction in which the cable is released from the gear shaft.

11. The holder according to claim 8, wherein, when the brake is disengaged from the gear, the brake is configured to allow the gear to rotate in a clockwise or counterclockwise direction so that the cable is wrapped around or released from the gear shaft.

12. The holder according to claim 1, further comprising:
    a wire that that traverses through the plurality of interconnected links in the link assembly, the wire configured to maintain a shape of the link assembly.

13. The holder according to claim 1, wherein the plurality of interconnected links are interconnected by a panel, the panel configured to have an elasticity associated therewith.

14. The holder according to claim 1, wherein the link assembly includes a first group of interconnected links connected to a first one of a left side and a right side of the holder main body and a second group of interconnected links connected to a second one of the left side and the right side of the holder main body.

15. A walking assistance robot configured to assist a user with walking, the walking assistance robot comprising:
    a walking assistive device having an exoskeleton shape such that the walking assistive device is configured to attach to one or more legs of the user via at least one holder, wherein the at least one holder includes,
    a plurality of interconnected links configured to attach to the one or more legs of the user, the plurality of interconnected links having an inner side surface facing the one or more legs of the user and an outer side surface facing a direction opposite the inner side surface, the plurality of interconnected links being pivotably connected by pins at the outer side surface;
    a cable configured to adjust an angle between adjacent ones of the plurality of interconnected links in response to tension applied thereto; and
    a tension device configured to apply the tension to the cable, wherein the inner side surface of each of the plurality of interconnected links is a same first distance from the cable while a second distance between the outer side surface of each of the plurality of interconnected links and the cable gradually decreases from a first link of the plurality of interconnected links to an end link of the plurality of interconnected links, the tension device including one of,
        a gear having a shaft extending therefrom, the gear connected to an adjuster, the tension device configured to vary an amount of tension applied to the cable by winding the cable around the shaft in response to the user manipulating the adjuster, and
        a processor and a sensor, the processor configured to instruct a driver to vary the amount of tension applied to the cable based on data from the sensor.

16. The walking assistance robot of claim 15, wherein
    the sensor is configured to detect when the user is walking; and
    the processor is configured to instruct the driver to vary the amount of tension applied to the cable based on whether the user is walking.

17. The walking assistance robot of claim 15, wherein the tension device is configured to apply the tension such that a net torque applied to the plurality of interconnected links is in equilibrium, the net torque including a force associated with the tension and a force associated with a counter force applied by the one or more legs of the user.

18. The walking assistance robot of claim 17, wherein the at least one holder is configured to apply the force associated with the tension to the one or more legs of the user such that the force associated with the tension is applied uniformly around a circumference of the one or more legs of the user.

* * * * *